United States Patent [19]

Cooper et al.

[11] Patent Number: 4,618,696
[45] Date of Patent: Oct. 21, 1986

[54] 9-OXO-15α-HYDROXY-16-PHENOXY AND 16-SUBSTITUTED PHENOXY 17,18,19,20-TETRANORPROSTA-4,5,13,(E)-TRIENOATES

[75] Inventors: Gary F. Cooper, Menlo Park; John A. Edwards, Los Altos, both of Calif.; Albert R. Van Horn, Boulder, Colo.

[73] Assignee: Syntex (U.S.A.) Inc., Palo Alto, Calif.

[21] Appl. No.: 636,058

[22] Filed: Jul. 31, 1984

[51] Int. Cl.⁴ .......................................... C07C 177/00
[52] U.S. Cl. ...................................... 560/53; 562/464
[58] Field of Search ........................ 560/53; 562/464; 514/530, 568

[56] References Cited
U.S. PATENT DOCUMENTS
4,178,457 12/1979 Van Horn ............................. 560/53

Primary Examiner—Paul J. Killos
Attorney, Agent, or Firm—Charles L. Hartman; Tom M. Moran; Alan M. Krubiner

[57] ABSTRACT

This invention covers a compound of the formula

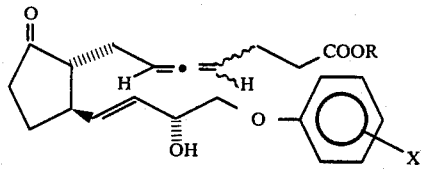

wherein R is hydrogen, lower alkyl or a pharmaceutically acceptable, non-toxic salt of a compound wherein R is hydrogen; and X is hydrogen, halo, trifluoromethyl, lower alkyl or lower alkoxy; and the wavy lines represent the α or β configuration with the proviso that when one wavy line is α the other is β.

8 Claims, No Drawings

9-OXO-15α-HYDROXY-16-PHENOXY AND 16-SUBSTITUTED PHENOXY 17,18,19,20-TETRANORPROSTA-4,5,13,(E)-TRIENOATES

BACKGROUND OF THE INVENTION

The present invention relates to certain novel prostaglandin compounds which are 9-oxo-15α-hydroxy-16-hydroxy and 16-substituted-phenoxy-17,18,19,20-tetranorprosta-4,5,13(E)-treinoate derivatives.

More particularly, the present invention relates to an enantiomer or racemic mixture of 16-phenoxy and 16-(o, m or p)-substituted phenoxy prostaglandins represented by the following formula

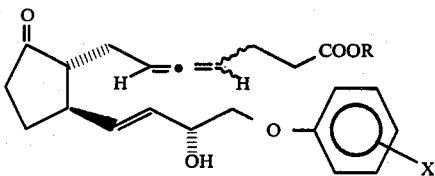

I wherein R is hydrogen, lower alkyl or a pharmaceutically acceptable, non-toxic salt of a compound wherein R is hydrogen; and X is hydrogen, halo, trifluoromethyl, lower alkyl or lower alkoxy; and the wavy lines represent the α or β configuration with the proviso that when one wavy line is α is the other is β.

In a second aspect, this invention relates to a process for making a compound of formula I which process comprises hydrolyzing with acid the $R^1$ group of a compound of the formula

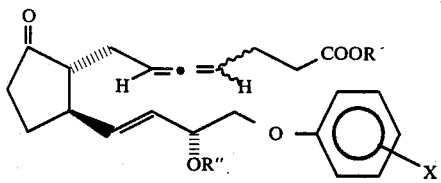

wherein R and X are defined above and $R^1$ is an ether-forming group.

DEFINITIONS

Formulas having an allene group are represented herein as having substituents on one end of the allene group which are oriented at 90° to those on the other. A broken line indicates that the substituent is behind the plane of the allene group and is designated as being in the α position. A triangular line defines the substituent as being in front of the plane of the allene group and is referred to as being in the β position. When there are at least three different groups substituted on the allene, as in formula I, the allene moiety is rendered asymmetric.

The broken lines shown in the above formula and other formulas herein at carbons 8, 9, 11 and 15 indicate that the pendent substituents are in the α configuration, i.e., below the plane of the cyclopentane ring or of the lower side chain. The triangular shaped line at C-12 denotes the β configuration, i.e. that the substituent is above the plane of the cyclopentane ring.

The double bond at C-13 in these formulas has the trans configuration the same as do the natural PGE and PGF series prostaglandins.

The compounds of this invention possess asymmetric centers and thus can be produced as racemic mixtures or as individual RS-antimers. The individual antimers may be obtained by resolving a racemic mixture of an intermediate at some appropriate stage of the synthesis. It is understood that the racemic mixtures and the individual RS-antimers are encompassed within the scope of the present invention.

For the sake of simplicity only one antimer, i.e., the antimer having the natural prostaglandin configuration will be depicted in the description of the process and claims; however, it is to be understood that the racemic mixtures and the individual unnatural antimers are also encompassed thereby, they being obtained by starting with the corresponding racemic mixture or unnatural antimer.

For the purpose of this invention, the terms "lower alkyl" or "alkyl" mean a straight or branched alkyl radical of 1 to 6 carbon atoms. Examples of such radicals are methyl, ethyl, propyl, isopropyl, butyl, t-butyl, i-butyl, sec-butyl, pentyl, hexyl and the like. Lower alkoxy means an —OR radical wherein R is lower alkyl. Halo refers to flouro, chloro, bromo and iodo. Aryl refers to phenyl, naphthyl or the like. Lower alkyl aryl refers to an aryl group having a lower alkyl chain wherein lower alkyl is defined above. Substituted lower alkyl aryl refers to a radical wherein the aryl group of a lower alkyl aryl is substituted with one or more lower alkyl, halo, or lower alkoxy radicals as these latter terms are defined above.

The term "pharmaceutically acceptable, non-toxic salts" refers to those base-derived salts of any compound herein having a carboxylic acid function. These salts are derived from pharmaceutically acceptable, non-toxic inorganic or organic bases.

Salts derives from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic, non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

The acid salts of these compounds, where appropriate to make, are prepared by treating the corresponding free acids of the compounds with at least one molar equivalent of a pharmaceutically acceptable base. Representative pharmaceutically acceptable bases are sodium hydroxide, potassium hydroxide, ammonium hydroxide, calcium hydroxide, trimethylamine, lysine, caffeine, and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, or dioxane. The molar ratio of compounds of formula I to base used are chosen to provide the ratio desired for any particular salt.

The numbering of these compounds follows that in use for the naturally occuring PGE and PGF compounds, illustrated as follows:

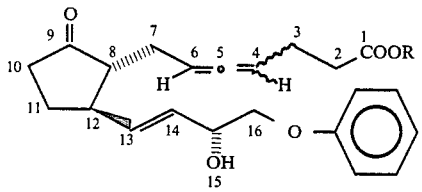

For analytical purposes, in this disclosure a carbon of a particular intermediate is identified by the number it will have in the final product, ie formula I. Thus, for example, in formula 8 in the Reaction Scheme below, the carbon on which the $R^2$ ether group is substituted is designated C-9 as that is the numbering of that carbon in formula I.

The compounds of the present invention exhibit prostaglandin-like biological activities and thus are used in the treatment of mammals where the use of prostaglandins is indicated. The compounds of the present invention are useful for the control of asthmatic attack because they are bronchodilators and they also exhibit anti-allergic properties by inhibition of mediator release. In addition, they are also useful in treating mammals for bronchial spasm or wherever bronchodilators are indicated. The compounds also exhibit vasodilator properties and are useful in controlling or palliating hypertension in mammals. They further exhibit central nervous system depressant activity in mammals, and are useful as sedatives.

The compounds of this invention also reduce gastric secretion, particularly gastric acid secretion and as such are useful in the therapy of ulcer diseases. These compounds are surprising more effective in reducing gastric acid secretion than is the compound methyl 9-oxo-11α,15α-dihydroxy-16-phenoxy-17,18,19,20-tetranor-prosta-4,5,13(E)-trienoate.

The present compound can be administered in a wide variety of dosage forms, either alone or in combination with other pharmaceutically compatible medicatiments in the form of pharmaceutical compositions suited for oral, parenteral or ophthalmic administration or inhalation in the case of bronchodilators. The pharmaceutical carrier can be either a solid material, liquid or aerosol, in which the compound is dissolved, dispersed or suspended, and can optionally contaim small amounts of preservatives and/or pH buffering agents.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dossages. Suitable solid carriers include, for example, pharmaceutical grades of starch, lactose, sodium saccharine, talcum, sodium bisulfite and the like.

Preferably, where the instant compounds are administered orally, the formulation will comprise a solvent in which these compounds are stable encapsulated in a soft, elastic gelatin capsule. Although the instant compounds are somewhat more stable that PGE-derived compounds having an 11-hydroxy group, it is preferred to formulate these compounds in a solvents which have been developed for use with PGE-type compounds to insure the long-term stability of the finished composition. Solvents known in the art to provide acceptable PGE-type formulations are for example ethanol, triacetin, propylene carbonate, dialkyl polyethylene glycols and the like. These solvents, and others of the same effect, are disclosed in U.S. Pat. Nos. 3,749,800; 3,826,823; 3,829,579; 3,852,052; 3,833,725; 4,221,793 and 4,410,545. Additional solvents suitable for the preparation soft, elastic gelatin formulations are refered to in these patents. This list of references is not intended to be exhaustive of those solvents which could be used in the SEG formulation of the instant compounds. Any solvent which gives an acceptable formulation life may be used.

The compounds of this invention are typically administered in dosages of about from about 0.001 µg. to about 100 µg. per Kg. of body weight. The precise effective dosage will, of course, vary depending upon the mode of administration, condition being treated and host. Thus, for example, to achieve bronchodilation about 1 µg. to about 10 µg. per Kg. of body weight is administered by aerosol, and to achieve inhibition of gastric secretions about 1 µg. to about 50 µg per Kg. of body weight is administered orally.

The process for preparing the instant compounds, including the novel intermediates is outlined in the following reaction scheme.

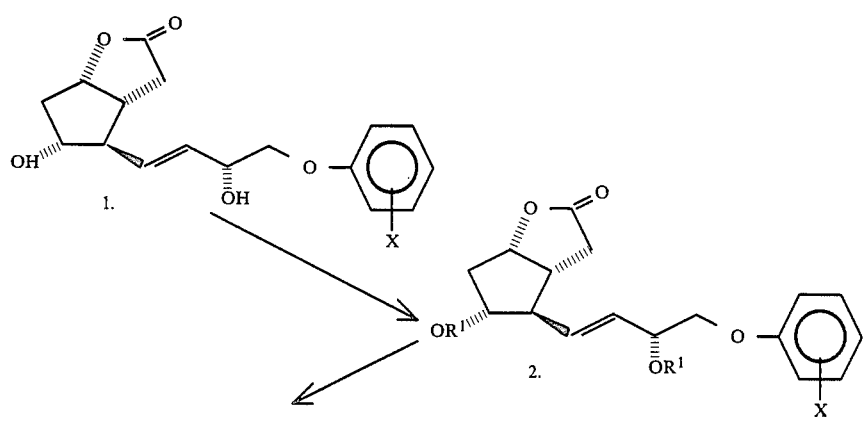

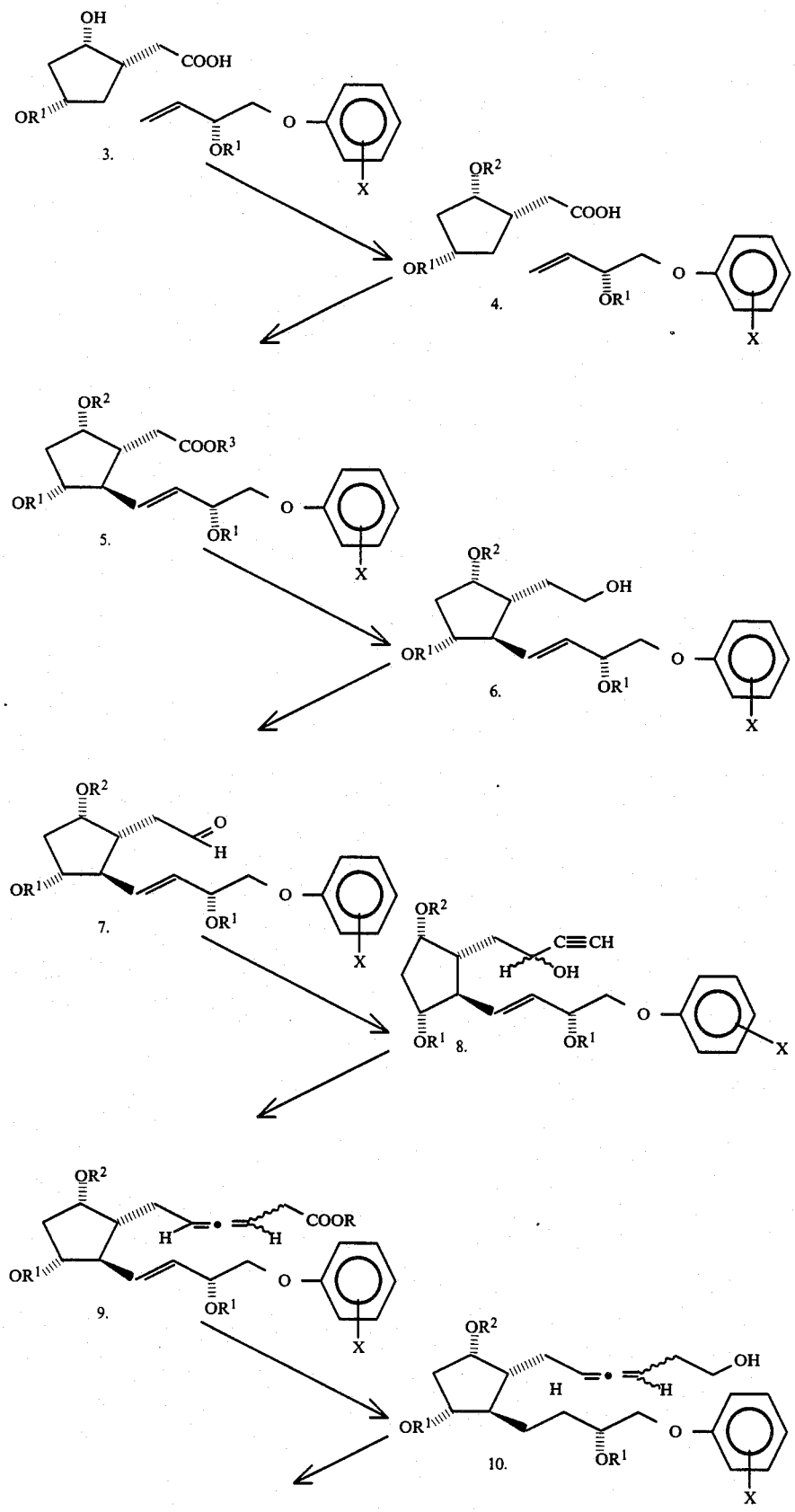

-continued
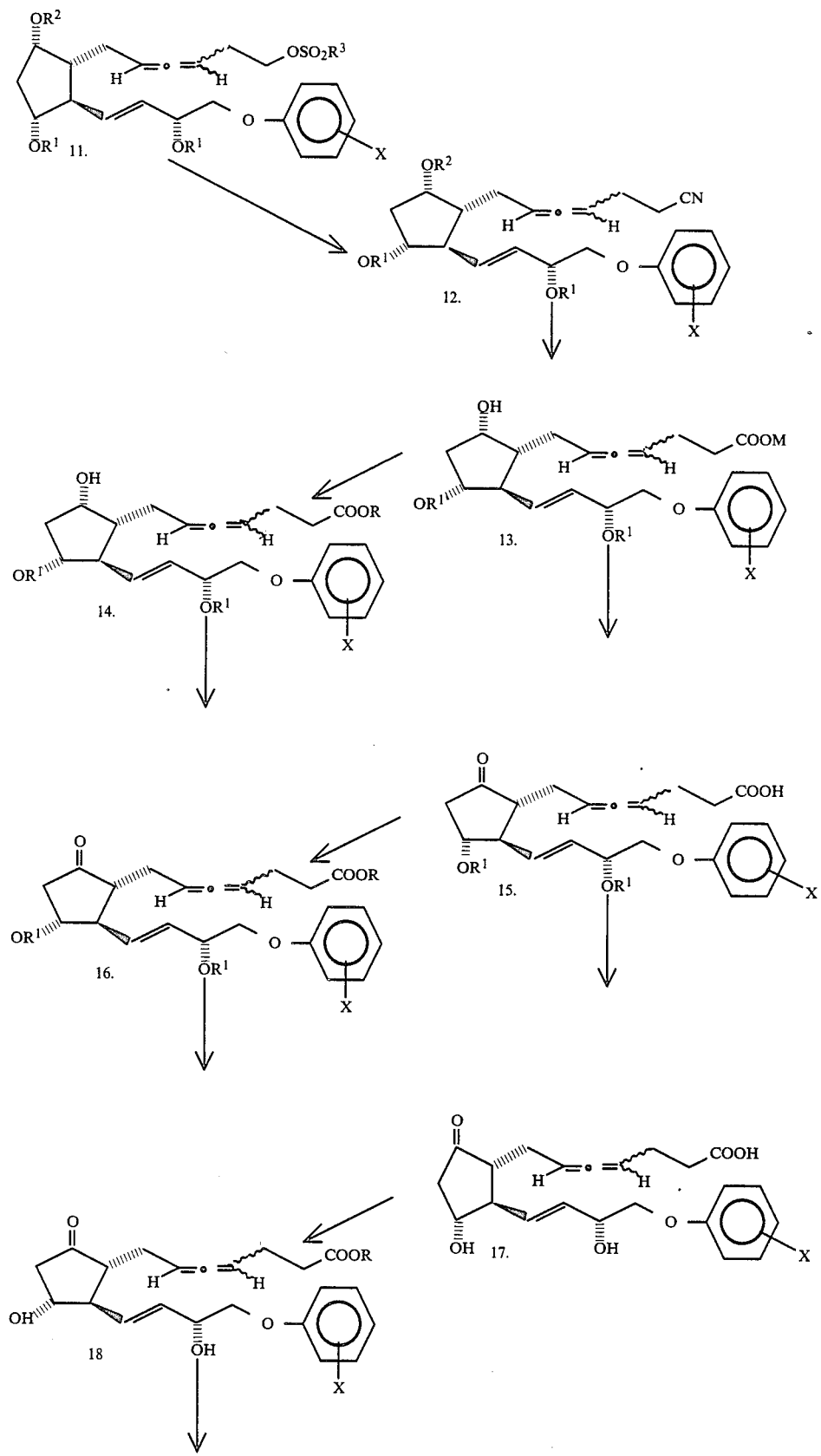

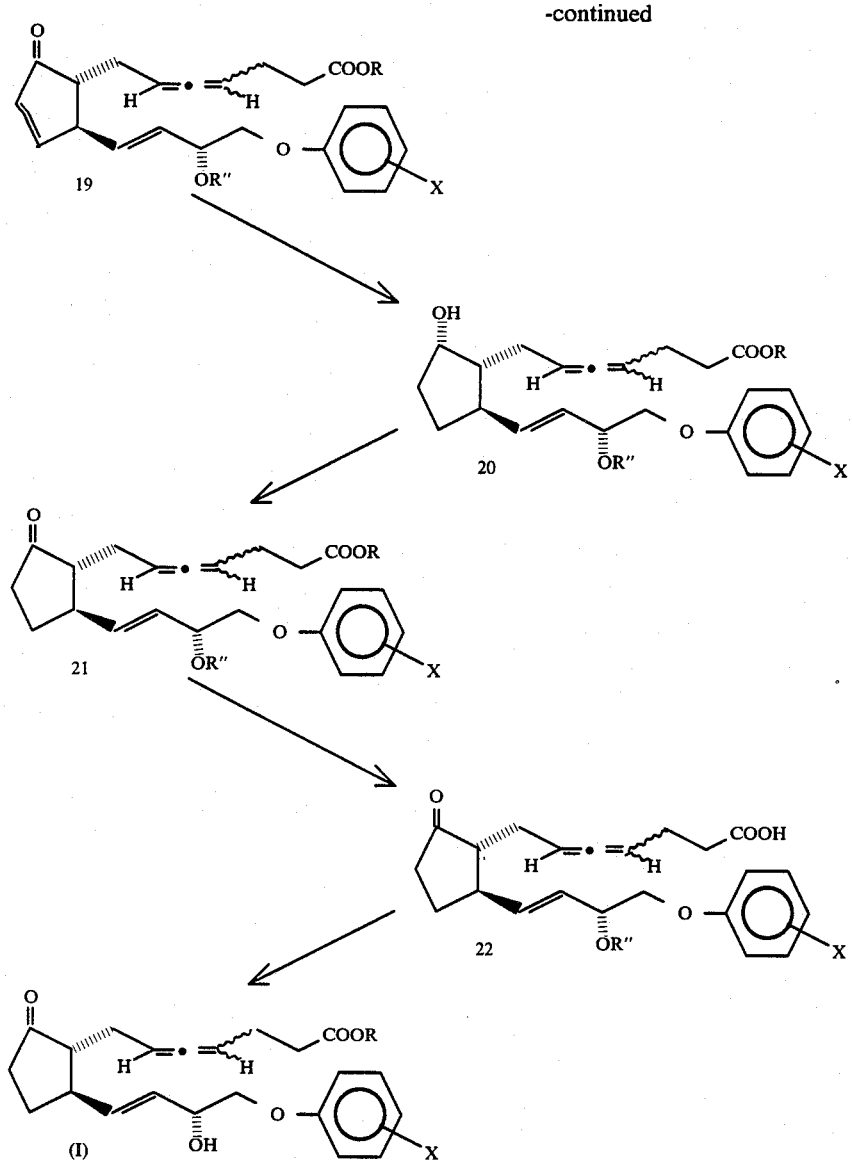

In the preceding schematics $R^1$ is a base-stabile, acid-labile ether-forming group, $R^2$ is a base-labile ether-forming radical, $R''$ is either $R^1$ or $R^2$ and M is hydrogen or a metal ion such as an alkali metal ion.

PREPARATIONS AND EXAMPLES

The starting material, formula 1, can be prepared according to the procedures set forth in U.S. Pat. Nos. 3,880,712, 3,985,791, and 4,304,907, which procedures are incorporated herein by reference and made a part hereof.

Before opening the lactone ring of formula 1, the two hydroxyl groups are converted to ethers. These two groups are designated $R^1$ and defined as base-stabile, acid-labile ether-forming groups. Such a group may be any ether-forming group which will not be hydrolyzed when treated with a strong aqueous base such a sodium or potassium hydroxide, yet will be hydrolyzed by acid under mild conditions, conditions which will not result in degradation of the product, formula I. Examples of groups which are base-stabile yet acid-labile are tetrahydrofuranyl, tetrahydropyranyl, 2-ethoxyethyl and the like. Excluded from this definition are alkyl ethers, benzyl ether and alkylaryl ethers, and the like. The conditions normally required to effect acid hydrolysis of these latter ethers would cause product degradation during the hydrolysis process, if in fact their hydrolysis would be effected by acid at all.

It is preferred to protect the C-11 and C-15 hydroxyl groups with tetrahydropyranyl, tetrahydrofuranyl or 2-ethoxyethyl. Ether formation with any of these groups is generally carried out in an aprotic solvent such as a halogenated hydrocarbon with an acid catalyst using amounts and conditions well known in the art. Most preferably, the ether-forming reagent will be dihydropyran, at least about 2.1 equivalents, the reaction being carried out in methylene chloride in the presence of p-toluenesulfonic acid. The reaction is generally carried out at between 20°–50° C., preferably at ambient temperature over a period of 15 minutes to four hours preferably about two hours.

Hydrolytic cleavage of the lactone ring is effected by means of a base, preferably an aqueous alkali metal base in a polar organic solvent. An aqueous solution of base such as lithium hydroxide, sodium hydroxide, potassium hydroxide, or the like, is added to a polar organic solvent containing the lactone, all under an inert atmosphere, e.g. nitrogen. The concentration of the added base preferably will be about 1–4M, more preferably between 2.8–3M. Potassium hydroxide is the preferred base. The aqueous base solution is added under nitrogen to a premade solution of the lactone in a solvent such as tetrahydrofuran or a simple alcohol such as methanol. The hydrolysis is effected by heating the solution at reflux under nitrogen, monitoring the reaction's progress by tlc.

The hydroxyl group generated by hydrolysis of the lactone is converted to an ether using a reagent which will give a base-labile ether. This group is designated $R^2$ and is defined as a base-labile ether-forming group. This group is best exemplified by —$SiR_4R_5R_6$ where $R_4$, $R_5$ and $R_6$ are alkyl, phenyl or arylalkyl except that all three may not be simultaneously methyl. For the purpose of this invention, alkyl means a radical of 1 to 6 carbon atoms. Arylalkyl is a radical wherein alkyl has the same meaning as lower alkyl and aryl is exemplified by but not limited to phenyl, alkyl substituted phenyl, and naphthyl, Particularly preferred silyl groups are t-butyldimethylsilyl, triiospropylsilyl, triphenylsilyl, t-butyldiphenylsilyl and 2,4,6-tri-t-butylphenoxydimethylsilyl radicals.

When a silylating agent is employed, standard conditions normally used for such a reagent are used. For example, the reaction is generally carried out in a polar aprotic solvent with an excess of the silylating reagent, 2.2 to 4 equivalents, and an excess relative to the silylating reagent of some nitrogen-containing compound such as imidazole.

Preferably, the imidazole and about 3 equivalents of t-butyldimethylsilyl chloride will be added to dry dimethylformamide solution of the hydroxy acid salt and stirred overnight at about room temperature, completion of the reaction being confirmed by tlc. This reaction gives the silyl ether as well as the silyl ester of the acid salt. Because the silyl ester is not desired, it is hydrolyzed in situ without being isolated by adding water to the reaction pot and then recovering the silyl ether compound in its free acid form.

The resulting free acid, represented by formula 4, is then converted to the aldehyde of formula 7. This can be accomplished by any number of appropriate methods, four of which are set out herein to exemplify the preferred methods. In one instance, formula 4 is esterified to give formula 5 which is then reduced to give the alcohol of formula 6, that being oxidized to the aldehyde of formula 7. A second alternative is to reduce the free acid of formula 4 to the alcohol of formula 6 and then oxidize the alcohol to the aldehyde (formula 7). Alternative three comprises esterifying the free acid of formula 4 and then reducing the ester directly to the aldehyde of formula 7. The fourth alternative is to first convert the free acid to the acid halide (acyl chloride) and then effect a Rosenmund reduction to form the aldehyde.

In the first alternative, the first step is to esterify the free acid by standard esterification procedures using, for example, either an alkyl iodide or a diazoalkane reagent. The words alkyl and alkane here have the same definition as that set forth above for lower alkyl.

When the reagent is an alkyl iodide, preferably methyl iodide, the reaction is carried out in an aprotic solent such as dimethylforamide or dimethylacetamide containing a weak base as sodium hydrogen carbonate. A large excess of the alkyl iodide is used, for example about 7–10 equivalents. The reaction is preferably carried out under an inert atmosphere, e.g. nitrogen and at a slightly elevated temperature not to exceed the boiling point of the alkyl iodide employed. If the reagent is methyl iodide, the reaction is preferably carried out at a temperature of about 40°–45° C. A number of hours are usually required to effect the reaction, usually 16 to 24 hours. Completion of the reaction is confirmed by tlc. If the reaction is not complete after the initial reaction period, an additional one equivalent aliquot of the alkyl iodide and a corresponding amount of base are added and the reaction continued as before. This procedure is repeated as often as necessary to complete the reaction.

If a diazoalkane is used, preferably diazomethane, the reaction is carried out using the standard procedures for generating the diazomethane and for reacting it with the free acid. See F. Arndt, Org. Syn. Coll. Vol II, 165 (1943) and H. vonPechmann, Chem. Ber. 27, 1888 (1894) and 28, 855 (1895).

In the second step of the first alternative, reduction of the carboxylic acid ester to the alcohol (formula 6) is effected by a metal hydride such as diisobutylaluminum hydride, lithium aluminum hydride or the like. The reaction is carried out in a solvent compatible with the selected reducing agent and preferably under an inert atmosphere and at a temperature of less than 50° C. for a period of up to about 4 hours.

When the reducing agent is diisobutylaluminum hydride, the reaction is carried out in toluene, benzene or a similar nonpolar solvent. The diisobutylaluminum hydride in toluene is added to a cooled solution (0°–10° C.) of the carboxylic acid ester after which the reaction solution is allowed to come to room temperature wherein the reaction is usually complete after 30–45 minutes. A nominal 2.5 equivalents of diisobutylaluminum hydride is employed to effect the reduction. The reaction is monitored by tlc and, if not complete, additional hydride is added and stirring continued for an another 30 minutes or so. Unreacted hydride is decomposed by adding water and an alkali metal salt such as sodium fluoride or sodium sulfate.

Alternatively, the carboxylic acid ester may be reduced to the alcohol using lithium aluminum hydride in a polar solvent such as ethyl ether, tetrahydrofuran or the like. Lithium aluminum hydride reduction is effected using the same ratio of materials and same reaction conditions are recited above for diisobutylaluminum hydride.

Oxidation of the alcohol to the aldehyde is carried out by means of a mild oxidizing reagent. Any one of a number of mild oxidizing reagents may be used to effect this oxidation but it is preferred to use chromium (VI) trioxide, pyridinium dichromate, pyridinium chlorochromate and the like but preferably chromium trioxide, in the presence of pyridine, hexamethylphosphoric triamide, 3,5-dimethylpyrazole and the like, preferably pyridine, or pyridinium chlorochromate with sodium acetate, and an organic solvent, e.g., dichloromethane, dichloroethane, and the like preferably, dichloromethane or mixtures thereof at a temperature from about −10° C. to about 30° C., preferably about 15° C. to about 25° C., for about 30 minutes to about 2 hours, preferably about 15 minutes to about 45 minutes, to obtain the aldehyde of formula 7. Advantageously, this reaction is carried out under anhydrous conditions under an inert atmosphere, e.g., nitrogen gas.

Alternative two is effected by simply reducing the free acid directly to the alcohol and then oxidizing that compound to the aldehyde of formula 7. The first step, reduction of the acid to the alcohol, is accomplished by means of borane methyl sulfide. In this reaction, the methyl ester is dissolved in a polar solvent, the solution stabilized in a bath at between about 0°–25° C. and the system purged with dry nitrogen. Borane methyl sulfide, about 3 equivalents is then added dropwise with stirring after which stirring is continued for up to about 6 hours, preferably about 3.5 hours to effect the reaction.

Having obtained the alcohol, it is then oxidized to the aldehyde in the manner set forth above for oxidizing formula 6 to formula 7.

The third alternative comprises first esterifying the free acid of formula 4 by the methods described above and then reducing the ester, formula 5, directly to the aldehyde by means of diisobutylaluminum hydride at low temperature. The reaction is effected using the same ratio of reactants given above, but in this instance the reaction is carried out at a temperature of about −70° C. or thereabouts.

In the fourth alternative, the free acid is reduced to the aldehyde by first converting the acid to its acid halide (chloride) and then carrying out a Rosenmund reduction or its equivalent.

Formation of the propargyl alcohols, formula 8, is effected by means of a metal acetylide in an appropriate anhydrous organic solvent such as a halogenated alkane, an ether, a hydrocarbon or the like, preferably under an inert atmosphere such as nitrogen. To a preformed solution of aldehyde in a solvent such as methylene chloride, dichloroethane, tetrahydrofuran, diethyl ether, toluene or the like, preferably methylene chloride, is added an excess of a metal acetylide reagent, exemplified by ethynyl magnesium chloride, ethynyl magnesium bromide, ethynyl magnesium iodide, lithium acetylide ethylene diamine complex and ethynyl lithium, under nitrogen. The preferred metal acetylide is ethynyl magnesium chloride. The reaction is carried out at a temperature between 0° and 50° C., preferably between 20°–30° C., until the reaction is complete as confirmed by tlc, usually within 30 minutes, most usually within 5–10 minutes.

The mixture of propargyl alcohol epimers may be separated into fractions containing a single pure propargylic epimer by chromatographic means, for example, silica gel tlc or column chromatography.

Conversion of the propargyl alcohol to the allene may be carried out by any reaction which effects a stereospecific homologation/rearrangement. By this means, a single propargyl alcohol epimer can be converted to a single corresponding allenyl isomer. Herein it is preferred to effect this rearrangement by means of a Claisen type rearrangement employing a trialkyl orthoacetate and a catalytic amount of a low molecular weight alkanoic acid, for example, acetic acid, propionic acid or the like. In this instance, a catalytic amount of acid is some amount less than 5% by volume relative to the volume of trialkyl orthoacetate.

The trialkyl orthoacetates which may be used are illustrated by trimethyl or triethyl orthoacetate and the like. The propargylic alcohol is dissolved in the trialkyl orthoacetate, preferably under nitrogen, along with a catalytic amount of alkanoic acid, usually about a 1% volume relative to the orthoacetate. The orthoester rapidly reacts with the propargyl alcohol to give a mixed trialkylorthoester which is not isolated but caused to rearrange in situ by heating the pot. The reaction flask is immersed in a preheated oil bath, for example one at about 150°–250° C., and stirred for a short period, about 30 minutes while maintaining the pot temperature between about 100°–130° C., preferably between about 110°–120° C. During the heating period, a mixture of orthoacetate and alkanoic acid, in the same ratio noted above, is added to the system while concurrently distilling out of the reaction system an equivalent volume of trialkyl orthoester-alkanol-acid. The reaction bath is preferably maintained at a temperature between about 170°–175° C. during the distillation process. The resulting product is the ester of formula 9.

To obtain the final product, it is necessary to add one carbon between the allene group and the acid function of formula 9 (homologation) in a manner which will not affect the stereochemistry of the allene or other sites on the molecule. The desired homologue is represented by formula 13. This homologation may be accomplished by a number of methods known in the art. The preferred methods employ a strong base in the last step of the homologation which will simultaneously cleave the $R^2$ group, giving the compounds of formula 13. Other reaction sequences require treatment with base after the homologue is formed in order to obtain the C-9 hydroxyl group of formula 13.

The alkyl ester generated by the Claisen rearrangement may be homologated by reducing the ester to its corresponding primary alcohol by some apropriate reducing reagent such as a metal hydride, e.g. lithium aluminum hydride, diisobutylaluminum hydride or the like. This alcohol is then converted to some functional group which is a good leaving group and then treated with an alkali metal cyanide, followed by treatment with a strong base to effect hydrolysis of both the nitrile and the $R^2$ group of C-9.

The leaving group to which the alcohol is converted may be, for example a halo group such as bromo or a sulfonyl ester. The alcohol is converted to the corresponding bromo compound by a variety of methods known in the art. This product is then treated with, for example sodium cyanide to make the nitrile. The nitrile is then hydrolyzed by strong base, which also serves to hydrolyze the $R^2$ base-labile ether group.

Alternatively, the alcohol is treated with an alkyl or arylalkyl sulfonyl ester forming reagent in preparation for making the nitrile. Such reagents are preferably methanesulfonyl chloride or p-toluenesulfonyl chloride or a similar sulfonyl halide. The sulfonyl ester is converted to the nitrile by means of an alkali metal cyanide salt, preferably sodium cyanide. This nitrile is then treated with strong base to effect formation of the acid while simultaneously hydrolyzing the $R^2$ group, which gives the compound of formula 13.

Another alternative is to reduce the ester function of formula 9 to an aldehyde, carry out a Wittig reaction, hydrolyze, and oxidize the resulting homologated aldehyde and then treat the resulting acid with base to effect hydrolysis of the $R^2$ group. In this sequence, the ester of formula 9 is reduced to its corresponding alcohol and oxided to the aldehyde. Alternatively, the ester may be reduced directly to the aldehyde using diisobutylaluminum hydride at low temperature, e.g. −70° C. The resulting aldehyde is then treated with the phosphorus ylide (phenyl)$_3$P=CHOCH$_3$ and then Hg(OAc)$_2$/HI to give the aldehyde homologue of formula 12. This aldehyde is treated with a mild oxidizing agent, one like the ones noted herein above, to obtain the protected acid. This protected acid is then treated with a dilute solution of a strong base to effect hydrolysis of the $R^2$ group. A full description of the base hydrolysis conditions is given herein below.

A third alternative is the Arndt-Eistert synthesis. For example, the ester is converted to the acid halide (chloride) by means of oxalyl chloride or thionyl chloride and then treated with diazomethane to give the diazoketone. The diazoketone is then rearranged to the homologated acid using silver oxide and water. This acid is then treated with base to hydrolyze the $R^2$ group giving the compound of formula 13.

The preferred method for converting formula 9 to its homologue, formula 13, is to first reduce the ester of formula 9 to its corresponding alcohol, form a sulfonyl ester of the alcohol, treat the sulfonyl ester with an alkali metal cyanide to obtain the nitrile, and convert the nitrile to the acid by base hydrolysis while simultaneously hydrolyzing the $R^2$ base-labile ether group.

In the preferred sequence, the acid ester of formula 9 is reduced to its corresponding alcohol by means of a metal hydride under anhydrous conditions, preferably under an inert atmosphere. A dry aprotic polar solvent such as absolute diethyl ether or the like is placed under a dry inert atmosphere and a reducing agent, for example a metal hydride such as lithium aluminum hydride (LAH) or the like, is added (2.2 to 4 equivalents) followed by the allenic ester. It is preferred to mix the several reaction ingredients at a reduced temperature, about 0°-15° C., and then reflux the solution for 10-30 minutes or until tlc indicates the reaction is complete.

When reduction is complete, the reaction mixture is again cooled to between 0°-15° C. and excess reagent (LAH) is reacted with a carbonyl-containing compound such as acetone or ethyl acetate thereby moderating subsequent and complete decomposition; complete decomposition follows addition of an aqueous complexing agent such as potassium sodium tartrate or a similar aluminum complex-forming salt.

In order to prepare the nitrile, the primary alcohol made as per the preceeding paragraph is first converted to a alkyl- or arylalkylsulfonyl ester, for example the methanesulfonyl ester or p-toluenesulfonyl ester derivatives. The allenyl alcohol, dissolved in an anhydrous polar organic solvent such as a halogenated alkane, i.e. methylene chloride, dichloroethane and the like is introduced into a reaction flask along with an anhydrous trialkylamine such as triethylamine. The reaction flask is purged with dry nitrogen and the reaction mixture cooled to between about −40° and 25° C. The sulfonyl ester-forming reagent, e.g. methanesulfonyl chloride, dissolved in the anhydrous organic solvent is then added with stirring while maintaining the temperature of the reaction mixture at between about −40° to −20° C., preferably between −30° to −20° C. About a two fold molar excess of the ester-forming reagent is used. When addition of the sulfonyl ester-forming reagent is completed, about 15-30 minutes, the reaction mixture is stirred at between about −30° to −10° C. until the reaction is complete as indicated by tlc. When the reaction is completed, the cooling bath is removed and additional trialkylamine is added, predissolved in the organic solvent. A solution of aqueous sodium bicarbonate or a similar base is then added with vigorous stirring in order to decompose excess ester-forming reagent.

The nitrile is formed by means of an alkali metal cyanide, preferably potassium cyanide. The reaction is carried out in a polar solvent, for example, dimethyl sulfoxide, under an inert atmosphere at a temperature between 50°-120° C. for up to an hour. Dry conditions are preferred.

The metal cyanide, about 5-8 equivalents, is first placed in a flask under an inert atmosphere such as nitrogen. Solvent is added and the flask placed in a bath preheated to about 75°-80° C. The intermediate, dissolved in the reaction solvent, is then added. Heating and stirring is continued for up to 2 hours, preferably 1 hour or until completion of the reaction as indicated by tlc.

Hydrolysis of the nitrile by base gives the acid salt, which may be neutralized to obtain the free acid, and at the same time deprotects the C-9 hydroxy group, which, as noted above is a base-labile ether. These hydrolyses are effected with a dilute solution of a strong base such as one of the alkali metal hydroxide bases, e.g. lithium hydroxide, sodium hydroxide, potassium hydroxide and the like. A dilute solution is one which has a concentration of 0.05 to 2M., preferably about 0.05M. An appropriate solvent is, for example, 2-methoxyethanol or a similar polar solvent which is miscible with water. Preferably, an inert atmosphere is maintained. In terms of temperature and time, the reaction is effected by heatein the solvent to reflux for up to about 72 hours.

Preferably these hydrolyses will be effected by charging a reaction flask with the solvent and reactant, adding the base, predissolved in water, and then purging the system with nitrogen. The reaction mixture is then refluxed for about 60 hours. The cooled reaction mixture is then neutralized before isolation of the 9-hydroxy-1-acid product.

The acid of formula 13 is esterified by the same procedures set forth herein above for esterifying formula 4.

Oxidation of the C-9 hydroxyl group is effected by a mild oxidizing agent such as those set forth herein above in the discussion relating to the oxidation of formula 6. Preferably, the oxidizing reagent will be chromium trioxide (4.5-10 equivalents) and 3,5-dimethylpyrazole or Collins reagent (chromium trioxide and pyridine), the reaction being carried out under an inert atmosphere in a polar aprotic solvent. Reagents are combined with solvent at reduced temperature, about −30° C. to −10° C. with stirring to effect thorough mixing of the reagents. The alcohol is then added in additional solvent, the initial reduced temperature being maintained during the addition and for the remainder of the reaction period, usually about 1 to 2 hours. Preferably the reaction will be carried out in methylene chloride under dry nitrogen for a period of about 1 hour.

Hydrolysis of the C-11 and C-15 blocking groups is effected by acid, for example, a alkanoic acid of 1 to 6 carbon atoms, referred to as a volatile fatty acid (VFA), or a hydrogen halide.

When acetic acid is used, standard procedures well known in the art may be used. For example, the standard hydrolysis procedure uses acetic acid and a polar solvent such a tetrahydrofuran or the like. The alkyl ester, glacial acetic acid, water and organic solvent are mixed in a flask under nitrogen and heated at low temperature, between about 20°-60° C., preferably 40° C. for up to 16 hours, preferably 12 hours.

Alternatively, hydrolysis of the ether groups may be effected by a hydrogen halide, preferably an aqueous solution of the acid dispersed in a water immiscible solvent, preferably with a scavenging agent to react with the released blocking groups, the reaction being effected at a temperature between −40° to 50° C. over a period of about 5 minutes to 4 hours. This method comprises stirring an aqueous solution of hydrogen halide with a water immiscible solvent in which the intermediate has been dissolved. The hydrogen halide may be hydrogen fluoride, hydrogen chloride, hydrogen bromide or hydrogen iodide. The acid should be present in a slight molar excess, for example about at least 2.05 equivalent of acid, though the reaction can be effected by using a large excess of acid, ie. up to 10 equivalents or more. Preferably 2.05 to 3.0 equivalents will be used, most preferably about 2.5 equivalents. Any water immiscible organic solvent may be used but it is preferred to use a halogenated hydrocarbon such as, for example, methylene chloride, dichloroethane and the like. To trap the released blocking group, a reactive scavenging material is added to the reaction mixture. This scavenging material is preferably a mercaptan, for example mercaptoethanol. The scavenging material is present in an amount of 2.0 to 3.0 equivalents, preferably about 2.0 equivalents. The reaction is complete in about 30–60 minutes at a temperature between about −30° to 50° C., preferably room temperature.

The compound of formula 19 is formed by dehydration of formula 18 using aqueous acid. Any mineral acid or water-soluble organic acid will effect this dehydration but it is preferred to use acetic acid herein. The compound is dissolved in an aqueous solution containing excess acid. The solution may then be heated to accelerate the dehydration, for example to about 65° C., for a period sufficient to effect complete dehydration. Usually the reaction is effected overnight. The product is then recovered by conventional means.

The 15α-hydroxy group is then protected by an acid-labile ether-forming group using the same reactants and conditions described herein above for converting formula 1 to formula 2.

The double bond, as well as the carbonyl group is then reduced by means of a metal hydride reducing agent in a dry solvent such as an alcohol (methanol) at room temperature or with heat. The reducing agent may be, for example a metal borohydride, lithium aluminum anhydride or the like. The reduction may be effected by heating the reaction solution of a steam bath for several hours, preferably about 3 hours. A ketone or some other appropriate carbonyl-containing compound is then added to consume excess reducing agent, after which the product is recovered by conventional means.

The 9-hydroxy compound from the preceding reaction is then oxidized with a mild, chromium-based oxidant in order to obtain the 9-oxo compound. The reaction is carried out under dry conditions and an inert atmosphere using a solvent such as methylene chloride. The oxidant is preferably chromium trioxide/3,5-dimethylpyrazole using standard amounts and conditions for this reaction. The reactants are combined at a reduced temperature, for example about −20° C. under nitrogen or another inert gas ina dry solvent such as mthylene chloride. The solution is stirred at the initial temperature for about one hour, then at room temperature for about another hour. The product is then recovered by conventional means.

The C-15 hydroxyl protecting group is then removed by acid following one of the two methods set out herein above for deprotecting formula 15 or 16.

Individual alkyl 9-oxo-15α-hydroxy-16-phenoxy-trienoate isomers were prepared by taking a single propargyl alcohol isomer of formula 10 and carrying that single isomer through the subsequent steps as set out herein above.

To further illustrate and exemplify the practice of this invention, the following non-limiting examples are provided.

EXAMPLE I (1α-Hydroxy-4α-(tetrahydropyran-2-yloxy)-3β-(3α-(tetrahydropyran-2-yloxy)-4-phenoxy-1(E)-buten-1-yl)cyclopent-2α-yl)acetic acid lactone A 1 liter round bottom flask equipped with a magnetic stirring bar and Drierite® drying tube was charged with 16.5 g of (1α,4α-dihydroxy-3β-(3α-hydroxy-4-phenoxy-1(E)-buten-1-yl)-cyclopent-2α-yl)-acetic acid lactone, 500 ml of methylene chloride, 8.8 ml of dihydropyran and a few crystals of p-toluenesulfonic acid.H$_2$O. This mixture was stirred at room temperature of 2 hours. Two drops of triethylamine were added and the solution stirred for 2 minutes. The reaction mixture was washed with 1×50 ml of saturated aqueous sodium chloride and dried over sodium sulfate. Evaporation of the solvent gave a residue which was taken up in a minimum amount of ethyl acetate and charged onto a 7.5 cm diameter column filled with 500 g of silica gel packed in pure hexane. The column was then eluted with a gradient of 20% to 40% ethyl acetate in hexane. Appropriate fractions were combined and stripped to dryness to afford the title compound.

Proceeding in a similiar manner, but substituting for the starting compound in the preceeding paragraph the appropriately substituted phenoxylactone, the following compounds may be prepared:

(1α-hydroxy-4α-(tetrahydropyran-2-yloxy)-3β-(3α-(tetrahydropyran-2-yloxy)-4-(m-trifluoromethylphenoxy)-1(E)-buten-1-yl)cyclopent-2α-yl)acetic acid lactone;

(1α-hydroxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-fluorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-fluorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-chlorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-chlorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-bromophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-bromophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-bromophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-methylphenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-methylphenyl)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-methylphenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-methoxyphenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-methoxyphenyl)-1(E)-buten-1-yl)-cyclopent-2α-yl)acetic acid lactone; and (1α-hydroxy-4α-(tetrahydropyran-2-yloxy)-3β-(3α-(tetrahydropyran-2-yloxy)-4-(p-methoxyphenoxy)-1(E)-buten-1-yl)-cyclopent-2α-yl)acetic acid lactone.

EXAMPLE 2

Potassium (1α-hydroxy-4α-(tetrahydropyran-2-yloxy)-3β-(3α-tetrahydropyran-2-yloxy)-4-phenoxy-1(E)-buten-1-yl)-cyclopent-2α-yl)-acetate A reaction flask equipped with a magnetic stirrer and reflux condenser topped with a nitrogen inlet was charged with 25 ml of tetrahydrofuran and 5 g of (1α-hydroxy-4α-(tetrahydropyran-2-yloxy)-3β-(3α-(tetrahydropyran-2-yloxy)-4-phenoxy-1(E)-buten-1-yl)-cyclopent-2α-yl)acetic acid lactone. The suspension was stirred until the reactant had dissolved during which time the flask was vacuum purged with nitrogen. An aliquot of 3.82 ml of 2.91M KOH/H₂O was added and the reaction flask again vacuum purged with nitrogen. This solution was then refluxed under nitrogen until the reaction was completed (monitored by tlc). The cooled solution was stripped to dryness, dissolved in 50 ml of toluene and stripped to dryness under vacuum to provide the title compound.

Proceeding in a similar manner, but replacing the starting material with an analog from Example 1, all compounds prepared as per Example 1 are converted to the corresponding potassium salt.

EXAMPLE 3

(1α-t-Butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-acetic acid A 7.76 g aliquot of potassium (1α-hydroxy-4α-(tetrahydropyran-2-yloxy)-3β-(3α-(tetrahydropyran-2-yloxy)-4-phenoxy-1(E)-buten-1-yl)-cyclopent-2β-yl)acetate was introduced into a reaction flask and 25 ml of dry dimethylformamide added. Imidazole, 4.32 g, was added to the stirred mixture followed by a 4.7 g aliquot of t-butyldimethylsilyl chloride. The reaction was stirred overnight at room temperature after which 5 ml of water was added with vigorous stirring for 30 to 45 minutes. The product was recovered by extraction with diethyl ether, followed by a saturated aqueous sodium chloride wash, after which the solution was dried over sodium sulfate and the solvent removed under reduced pressure. The residue was further purified by passing it through a 350 ml "C" sintered glass filter funnel packed with 95 g silica gel slurried in 10% v/v ethyl acetate/hexane, the free acid being eluted with 1 L of 10% ethyl acetate/hexane. Appropriate fractions were combined and the solvent removed to give the title compound.

By the same method, the compounds prepared in Example 2 are converted to the corresponding t-butyldimethylsilyl ether compounds.

EXAMPLE 4

Methyl (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetate Dry dimethylformamide, 80 ml, and 6.24 g of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetic acid, 3.00 g NaHCO₃ and 12.01 g methyl iodide were introduced into a reaction flask equipped with a stirrer and reflux condenser topped with N₂/vac/septum inlet. The flask was vacuum purged five times with nitrogen and then heated to between 40°–45° C. and stirred overnight. Additional methyl iodide (1.46 g) was added and the reaction continued at 40°–45° C. over a second night. Water, 500 ml, was then added to the reaction mixture which was then extracted with 3×50 ml of methylene chloride. The combined methylene chloride layers were further diluted with an equal volume of hexane. The resulting organic layer was washed with water (2×50 ml), saturated sodium chloride (1×50 ml) and dried over sodium sulfate. Evaporation of the solvent afforded a residue which was further purified by silica gel column chromatography. The silica gel was prepared in 15% ethyl acetate/hexane and the compound eluted with that solvent mixture. Combined fractions were stripped to dryness to give the captioned compound.

Proceeding in the same manner, but substituting for the starting compound named herein, the compounds prepared in Example 3, each compound prepared in that Example may be converted to its methyl ester.

EXAMPLE 5

(1α-t-Butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-2-ethan-1-ol Into a reaction flask fitted with a N₂/vac/septum was introduced 53 ml of dry toluene in which was dissolved 5.3 g of methyl (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetate. The reaction was cooled in an ice bath and vacuum purged five times with nitrogen. Using a dry syringe transfer technique, 21.4 ml of diisobutylaluminum hydride, 1.0M in toluene, was placed in an addition funnel and added to the cool reaction solution over about 20 minutes. The ice bath was then removed and the reaction mixture checked by tlc after 30 minutes. If the reaction was not complete an additional 4.28 ml of the hydride solution was added. When reduction was complete, the reaction mixture was diluted with 26 ml of dry hexane and 4.32 g of sodium fluoride powder was added with vigorous stirring. A 1.39 ml aliquot of water was then added with stirring. After an additional 30–40 minutes had elapsed, during which stirring was continued, the reaction solution was filtered through celite and rinsed with 100 ml methylene chloride. The solvent was then stripped off under vacuum and the residue further purified by silica gel column chromatography.

Proceeding in a similiar manner, compounds made in Example 4 may be transformed to their corresponding alcohol.

EXAMPLE 6

(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-2-ethan-1-ol The following process is an alternative method for making the captioned alcohol.

A 1.08 g aliquot of methyl (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetate was weighed into a round bottom flask equipped with a stirrer and septum/N$_2$/vacuum inlet. Dry tetrahydrofuran, 11 ml, was added to dissolve the acetate. The flask was placed in a water bath at about 18°–20° C. and purged five times with dry nitrogen. Then 0.392 ml of borane methyl sulfide was added dropwise over 30 minutes. Stirring was then continued for about 3.5 hours. Methanol, 1 ml, was then added dropwise, gas evolution being controlled by the rate of addition. An additional 5 ml of methanol was then added, the solution then being stirred for another 30 minutes. The reaction mixture was then concentrated. The residue was dissolved in methanol and reconcentrated. The second concentrate was dissolved in 25 ml of diethyl ether and washed with 1×5 ml of water, 1×5 ml of saturated aqueous sodium bicarbonate, 1×5 ml of brine and dried over sodium sulfate. This dried solution was filtered and concentrated, giving a colorless oil.

The oil from above was further purified by percolating it through a column of 10 g of silica gel packed wet in 10% ethyl acetate/hexane. The product was eluted with successive portions of 200 ml 10% ethyl acetate/hexane, 200 ml of 20% ethyl acetate/hexane and 200 ml of 30% ethyl acetate/hexane while collecting 20 ml fractions. Fractions 12–30 were combined and the solvent removed in vacuo, giving the captioned product as a colorless oil.

EXAMPLE 7

(1α-t-Butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetaldehyde A reaction flask was fitted with an addition funnel and dry nitrogen inlet/outlet valves. 150 ml of anhydrous methylene chloride and 5.96 g of anhydrous chromium (VI) trioxide was placed in the flask. The flask was vacuum purged with dry nitrogen and cooled in an ice bath to approximately 15° C. To the flask was then added with vigorous stirring 9.46 g of anhydrous pyridine after which the reaction mixture was stirred vigorously under dry nitrogen at ambient temperature for 30 minutes. Dry celite (5.0 g) was then added under nitrogen followed by 4.7 g of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-2-ethan-1-ol in 18.5 ml of anhydrous methylene chloride. The reaction solution was stirred for 15–20 minutes, or until tlc indicated the reaction was complete, at which time 12.5 g of pulverized sodium hydrogen sulfate monohydrate was added. After an additional 15 minutes of vigorous stirring, the reaction mixture was filtered and the retentate washed with methylene chloride (3×50 ml). The combined methylene chloride solutions were washed with 3×50 ml of water and the aqueous layer back extracted with 2×25 ml methylene chloride. The dried (anhydrous sodium sulfate) methylene chloride solution was stripped under vacuum to provide the captioned compound.

By this means, the compounds prepared in the Examples 5 and 6 are converted to their corresponding acetaldehyde as illustrated by the following compounds:

(1α-t-butyldimethylsilyloxy-4α-(tetrahydropyran-2-yloxy)-3β-(3α-(tetrahydropyran-2-yloxy)-4-(m-trifluoromethylphenoxy)-1(E)-buten-1-yl)-cyclopent-2α-yl)-acetaldehyde;

(1α-t-butyldimethylsilyloxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-fluorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(p-fluorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(p-chlorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-chlorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-bromophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-bromophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(p-bromophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(p-methylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-methylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-methylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-methoxyphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-methoxyphenoxy)-1(E)-buten-1-yl)-cyclopent-2α-yl)acetaldehyde; and (1α-t-butyldimethylsilyloxy-4α-(tetrahydropyran-2-yloxy)-3β-(3α-(tetrahydropyran-2-yloxy)-4-(p-methoxyphenoxy)-1(E)-buten-1-yl)-cyclopent-2α-yl)acetaldehyde.

EXAMPLE 8

(1α-t-Butyldimethylsilyloxy-4α-(tetrahydropyran-2-yloxy)-3β-(3α-(tetrahydropyran-2-yloxy)-4-phenoxy-1(E)buten-1-yl)-cyclopent-2α-yl)acetaldehyde Alternatively, the captioned aldehyde can be made directly from the methyl ester of Example 4 by means of the following reaction. A 100 mg aliquot of methyl-(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetate was weighed into a round bottom flask fitted with a stirrer and septum/N$_2$/vaccuum inlet. Toluene, 1 ml, was added and the system vacuum purged with N$_2$ five times. This solution was cooled in a dry ice/isopropanol bath and 0.324 ml of 1M diisobutylaluminium hydride in toluene added was added dropwise over about 8 minutes. This solution was stirred under nitrogen at −78° C. for 2 hours and then diluted with 10 ml of diethyl ether. The cold bath was removed and 4 ml of saturated aqueous ammonium chloride added, the resulting solution being stirred vigorously for 30 minutes and then filtered through celite. The aqueous layer was extracted with diethyl ether, the extracts were combined, dried, and the solvent removed in vacuo to give the aldehyde as an oil.

This reaction may be used to convert any other methyl ester prepared in Example 4 to its corresponding aldehyde, as illustrated by the following compounds:

(1α-t-butyldimethylsilyloxy-4α-(tetrahydropyran-2-yloxy)-3β-(3α-(tetrahydropyran-2-yloxy)-4-(p-hexylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-hexylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-hexylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-hexyloxy-phenoxy)-1(E)-buten-1-yl)-cyclopent-2α-yl)-acetaldehyde;

(1α-t-butyldimethylsilyloxy-4α-(tetrahydropyran-2-yloxy)-3β-(3α-(tetrahydropyran-2-yloxy)-4-(o-hexyloxy-phenoxy)-1(E)-buten-1-yl)-cyclopent-2α-yl)-acetaldehyde; and (1α-t-butyldimethylsilyloxy-4α-(tetrahydropyran-2-yloxy)-3β-(3α-(tetrahydropyran-2-yloxy)-4-(p-hexyloxy-phenoxy)-1(E)-buten-1-yl)-cyclopent-2α-yl)-acetaldehyde.

EXAMPLE 9

(1α-t-Butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-1-but-3-yn-2-ol To a reaction flask fitted with a pressure equalizing addition funnel and dry nitrogen inlet/outlet valves was added 4.65 gm (7.9 mM) of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetaldehyde in 30 ml of anhydrous methylene chloride. The flask was vacuum purged with dry nitrogen and cooled to approximately 15° C. while stirring vigorously. To this solution was added 9.0 ml of a 1.25M ethynyl magnesium chloride solution in tetrahydrofuran after which the pot was stirred for 5–10 minutes at ambient temperature or until the reaction was complete as indicated by tlc. Then 30 ml of methylene chloride and 50 ml of warm (35° C.) filtered, saturated aqueous ammonium chloride was added and the solution stirred vigorously for 5–10 minutes. A 50 ml aliquot of warm water (35° C.) was added with an additional 5–10 minute stirring time. This solution was then filtered and the retentate washed with 50 ml of methylene choride and the aqueous layer extracted with 2 additional 15 ml portions of methylene chloride. The combined methylene chloride extracts were mixed with 100 ml of water, the methylene chloride layer being removed and the aqueous layer back-extracted with 20 ml of methylene chloride. The combined methylene chloride solutions were dried over anhydrous sodium sulfate, filtered and the solvent removed under reduced pressure to afford the captioned compound as an oily residue.

The individual isomers may be separated as follows: the oil from above was chromatographed on silica gel made up in hexane, the product being eluted with 5%–15% ethyl acetate/hexane in 5% step increments of ethyl acetate. This separation technique afforded two fractions, each comprising a stereochemically pure propargyl alcohol.

A $^{13}$C NMR spectrum was measured for the purified, but unseparated mixture of the two stereoisomers of (1α,4α-dihydroxy-3β-(3α-hydroxy-4-phenoxy-1(E)-buten-1-yl)-cyclopent-2α-yl)-1-but-3-yn-2-ol and for the two individual isomers after chromatographic separation. The protecting groups at C-9, C-11 and C-15 were hydrolyzed by acid before measuring the NMR spectra. Acid hydrolysis was effected by acetic acid using the conditions and reagents set out below in Example 17 though the reagents and conditions of Example 18 could also be used for this purpose. The spectra were measured in CDCl$_3$/CD$_3$OD on a Bruker WM 300 spectrometer operating at 75.473 MHz using a spectral width of 18,500 Hz, 40° flip angles and 16K data tables, zero filled to 32K after application of a 1.0 Hz line broadening giving a digital resolution in the frequency domain of 0.03 ppm. Tetramethylsilane was used as the internal standard for all spectra.

The resulting spectral data are set out in the following charts. The chemical shift is given for each carbon in the formula. Numbers 1 to 16 signify the particular carbon in question relative to formula I. Numbers 17 to 20 signify the oxygen-substituted, ortho, meta and para carbons respectively of the phenoxy moiety. In this Example the first three carbons are not present so there is no chemical shift recorded, designated by the letters NA for "not applicable." The separated isomers are designated "1" and "2" solely for the purpose of identification.

|    | ISOMER MIXTURE | ISOMER 1 | ISOMER 2 |
|----|----------------|----------|----------|
| 1. | NA             | NA       | NA       |
| 2. | NA             | NA       | NA       |
| 3. | NA             | NA       | NA       |
| 4. | 72.68, 73.39   | 73.36    | 72.54    |
| 5. | 84.38, 85.17   | 84.27    | 85.18    |

-continued

| | ISOMER MIXTURE | | ISOMER 1 | ISOMER 2 |
|---|---|---|---|---|
| 6. | 60.65, | 61.37 | 60.69 | 61.36 |
| 7. | 34.28, | 35.71 | 34.20 | 35.71 |
| 8. | 45.42, | 47.33 | 45.55 | 47.43 |
| 9. | 71.84, | 71.96 | 71.89 | 71.94 |
| 10. | 42.10, | 42.19 | 42.01 | 42.10 |
| 11. | 76.86, | 76.95 | 77.03 | 76.85 |
| 12. | 55.47, | 55.76 | 55.64 | 55.82 |
| 13. | 130.89 | | 130.70 | 130.86 |
| 14. | 134.86, | 134.95 | 134.92 | 134.86 |
| 15. | 70.90, | 70.97 | 70.92 | 70.87 |
| 16. | 71.65 | | 71.64 | 71.66 |
| 17. | 158.56 | | 158.54 | 158.57 |
| 18. | 114.75 | | 114.70 | 114.75 |
| 19. | 129.56 | | 129.56 | 129.56 |
| 20. | 121.20 | | 121.20 | 121.21 |

By using the same reagents and conditions and repeating the chromatographic separation outlined here, the acetaldehydes prepared in Examples 7 and 8 are converted to the corresponding alcohol and may be separated into the individual stereoisomers. The following list of compounds illustrates some of these compounds:

(1α-t-butyldimethylsilyloxy-4α-(tetrahydropyran-2-yloxy)-3β-(3α-(tetrahydropyran-2-yloxy)-4-(m-trifluoromethylphenoxy)-1(E)-buten-1-yl)-cyclopent-2α-yl)-1-but-3-yn-2-ol;

(1α-t-butyldimethylsilyloxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-fluorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-fluorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-chlorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-chlorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-bromophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-bromophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-bromophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-methylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-methylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-methylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-methoxyphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-methoxyphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-methoxyphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-hexylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-hexylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-hexylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-hexyloxy-phenoxy)-1(E)-buten-1-yl)-cyclopent-2α-yl)-1-but-3-yn-2-ol;

(1α-t-butyldimethylsilyloxy-4α-(tetrahydropyran-2-yloxy)-3β-(3α-(tetrahydropyran-2-yloxy)-4-(o-hexyloxy-phenoxy)-1(E)-buten-1-yl)-cyclopent-2α-yl)-1-but-3-yn-2-ol; and (1α-t-butyldimethylsilyloxy-4α-(tetrahydropyran-2-yloxy)-3β-(3α-(tetrahydropyran-2-yloxy)-4-(p-hexyloxy-phenoxy)-1(E)-buten-1-yl)-cyclopent-2α-yl)-1-but-3-yn-2-ol.

EXAMPLE 10

Ethyl-(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-hexa-3,4-dienoate A three necked flask was fitted with a nitrogen inlet needle, pressure equalized addition funnel and vacuum type distillation head fitted with a cold finger condenser. A solution of 3.18 g of one isomer of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-1-but-3-yn-2-ol in 18 ml of triethyl orthoacetate, to which was added 0.18 ml of glacial acetic acid, was introduced into the reaction vessel. Dry nitrogen was bubbled through the reaction solution which was heated with stirring in a 170°–175° C. oil bath. Over a period of 30–35 minutes an additional 0.1 ml of glacial acetic acid and 6.0 ml of triethyl orthoacetate was added to the reaction solution. A 6 ml volume of triethyl orthoacetate-ethanol-acetic acid was distilled out of the reaction system after which the hot reaction solution was transferred to a second flask and 12.0 ml of toluene added to the reaction solution. The reagents were then distilled off under reduced pressure to give an oil. Toluene was added to this oil after which the toluene was removed under reduced pressure to afford the captioned compound. The crude allenyl ester was then chromatographed on silica gel eluting with a gradient of hexane to 50% ethyl acetate/hexane to separate the allene from its propargyl alcohol precursor.

Proceeding in the same manner, each of the individual isomers, or an unseparated mixture, of the compounds prepared in Example 7 and 8 are stereospecifically rearranged to their corresponding dieneoate illustrated by the following compounds:

ethyl-(1α-t-butyldimethylsilyloxy-4α-(tetrapyran-2-yloxy)-3β-(3α-(tetrahydropyran-2-yloxy)-4-(m-trifluoromethylphenoxy)-1(E)-buten-1-yl)-cyclopent-2α-yl)-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-fluorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-fluorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-fluorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-chlorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-chlorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-chlorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-bromophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-bromophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-bromophenoxy)-1(E)-buten-1-yl)-cyclopent-2α-yl)1-6-hexa-3,4-dienoate;

ethyl-(1αt-butyldimethylsilyloxy-4α-(tetrapyran-2-yloxy)-3β-(3α-(tetrahydropyran-2-yloxy)-4-(p-methylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-methylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-methylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-methoxyphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-methoxyphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-methoxyphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-hexylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-hexylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-hexylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-hexyloxy-phenoxy)-1(E)-buten-1-yl)-cyclopent-2α-yl)-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-hexyloxy-phenoxy)-1(E)-buten-1-yl)-cyclopent-2α-yl)-6-hexa-3,4-dienoate; and ethyl-(1α-t-butyldimethylsilyloxy-4α-(tetrapyran-2-yloxy)-3β-(3α-(tetrahydropyran-2-yloxy)-4-(p-hexyloxy-phenoxy)-1(E)-buten-1-yl)-cyclopent-2α-yl)-6-hexa-3,4-dienoate.

EXAMPLE 11

(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-hexa-3,4-dien-1-ol To a three neck reaction flask fitted with a thermometer, pressure equalization addition funnel, dry nitrogen inlet and vacuum outlet was added 62.5 ml of absolute diethyl ether; the reaction system was then purged using dry nitrogen. There was then added, in portions, under a dry nitrogen atmosphere with stirring, 0.32 g of powdered lithium aluminum hydride. The solution was stirred for 15–20 minutes at ambient temperature and then cooled to about 10° C. A solution of 6.56 g of ethyl-(1α-t-butyldimethylsilyloxy-4α-(tetrahydropyran-2-yloxy)-3β-(3α-(tetrahydrpyran-2-yloxy)-4-phenoxy-1(E)-buten-1-yl)-cyclopent-2α-yl)-6-hexa-3,4-dienoate in 23.5 ml of absolute diethyl ether was added at a rate which maintained the temperature between 10°–15° C. The reaction mixture was then stirred at room temperature until the reduction was complete, then again cooled to about 10° C. and 3.0 ml of acetone added over about 15 minutes after which the reaction pot was stirred for an additional 15 minutes. There was then added dropwise 2.5 ml of saturated aqueous potassium sodium tartrate. When there was no more evolution of hydrogen gas, an additional 29.0 ml of saturated aqueous sodium potassium tartrate was added, the reaction pot being at ambient temperature. The aqueous phase was recovered and extracted with 2×25 ml of ethyl acetate. The combined ethereal and ethyl acetate extracts were washed with 35 ml of water. The organic layer was then dried over anhydrous sodium sulfate, filtered and concentrated in vacuo to give the title alcohol.

These same reagents and conditions will reduce any of the dienoate compounds prepared in Example 10 above to the corresponding alcohol.

EXAMPLE 12

(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-(1-methansulfonyloxy)-hexa-3,4-diene To a reaction flask fitted with nitrogen inlet/outlet valves and mechanical stirrer was added 7.24 g of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-hexa-3,4-dien-1-ol in 67 ml of anhydrous methylene chloride. To this was added 6.7 ml of anhydrous triethylamine at which time the system was purged with dry nitrogen and cooled to about −30° C. There was then added 2.35 g of methanesulfonyl chloride in 13.5 ml of anhydrous methylene chloride over a 15–20 minute period while maintaining the reaction solution at its initial temperature. The reaction mixture was then stirred until the reaction was complete, about 30 minutes. The cooling bath was removed and a solution of 2.0 ml of triethylamine in 20 ml of methylene chloride was added followed by 20 ml of saturated, aqueous sodium bicarbonate. The methylene chloride layer was recovered and the aqueous layer extracted with 2×50 ml of methylene chloride. The combined methylene chloride extracts were washed with 20 ml of saturated sodium bicarbonate-water (1:1-V:V). The organic layer was dried over anhydrous sodium sulfate and solvents removed under reduced pressure to yield the captioned compound.

Proceeding in this manner, but substituting for the recited dienol, any of the other dienols which are prepared by the method of Example 11, such deinols may be converted to their corresponding mesylates.

EXAMPLE 13

(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-hexa-3,4-dieno-1-nitrile To a flask fitted with dry nitrogen inlet/outlet valves was added 4.7 g of potassium cyanide and 16.5 ml of anhydrous dimethylsulfoxide. This mixture was stirred under dry nitrogen at 75°–80° C. for about 30 minutes. There was then added, in one portion, a solution of 8.13 g of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-(1-methansulfonyloxy)-hexa-3,4-diene in 20 ml of anhydrous dimethylsulfoxide. The reaction was continued for about 60 minutes in the 60°–80° C. bath in order to effect completion of the reaction. The reaction solution was then cooled to about 40° C. and 5 ml of methylene chloride added. This mixture was then further cooled to ambient temperature and transferred to a separatory funnel containing 120 ml of methylene chloride. The reaction flask was washed with methylene chloride, the washes being transferred to the extraction funnel. The methylene chloride solution of crude nitrile was shaken with 160 ml of water whereupon the upper aqueous phase was recovered and extracted with 3×40 ml of methylene chloride. The combined methylene chloride extracts were washed with 120 ml of water. The combined aqueous phases were then again extracted with 40 ml of methylene chloride. All methylene chloride extracts were combined and dried over anhydrous sodium sulfate, filtered, and the solvent removed under reduced pressure to yield the captioned compound. The crude nitrile was further purified by passing the crude oil through a silica gel column, eluting with a hexane/50% ethyl acetate-hexane gradient to give fractions of the captioned compound.

The other mesylates, or a similar sulfonyl ester, prepared in Example 12 may be converted to their corresponding nitrile by the foregoing method as illustrated by the following compounds:

(1α-t-butyldimethylsilyloxy-4α-(tetrapyran-2-yloxy)-3β-(3α-(tetrahydropyran-2-yloxy)-4-(m-trifluoromethylphenoxy)-1(E)-buten-b 1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-fluorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-fluorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-fluorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-chlorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-chlorophenoxy)-3(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-chlorophenoxy)-1(E)-buten-1-yl)-cyclopent-2-α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-bromophenoxy)-1(E)-buten-1-yl)-cyclopent-2α-yl)-6-hexa-3,4-dieno-1-nitrile;

(1α-t-butyldimethysilyloxy-4α-(tetrapyran-2-yloxy)-3β-(3α-(tetrahydropyran-2-yloxy)-4-(o-bromophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-bromophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-methylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-methylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-methylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-methoxyphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-methoxyphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-methoxyphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-hexylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-hexylphenoxy)-1(E)-buten-1-yl)-cyclopent-2α-yl)-6-hexa-3,4-dieno-1-nitrile;

(1α-t-butyldimethoxysilyloxy-4α-(tetrapyran-2-yloxy)-3β-(3α-(tetrahydropyran-2-yloxy)-4-(m-hexylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-hexyloxyphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-hexyloxyphenoxy)-1(E)-buten-1-yl)-cyclopent-2α-yl)-6-hexa-3,4-dieno-1-nitrile; and (1α-t-butyldimethylsilyloxy-4α-(tetrapyran-2-yloxy)-3β-(3α-(tetrahydropyran-2-yloxy)-4-(p-hexyloxyphenoxy)-1(E)-buten-1-yl)-cyclopent-2α-yl)-6-hexa-3,4-dieno-1-nitrile.

EXAMPLE 14

Methyl 9α-hydroxy-11α,15α-bis-(tetrahydropyran-2-yloxy)-16-phenoxy-17,18,19,20-tetranorprosta-4,5,13(E)-trienoate A reaction flask fitted with a condenser and nitrogen inlet/outlet valves was charged with 3.47 g of the 1-nitrile from Example 13 dissolved in 37.0 ml of 2-methoxyethanol. To this was added a solution of 0.9 g of potassium hydroxide in 3.1 ml of water after which the system was vacuum purged with dry nitrogen. The reaction was then heated at reflux under nitrogen for approximately 63 hours. The reaction mixture was then cooled to about 50°–60° C. and the solvents removed under reduced pressure. The residue was dissolved in 5.0 ml of water and transferred to a reaction flask equipped with a pressure equalization addition funnel and pH electrode. The solution was cooled to between 5°–10° C. and cool (10° C.) aqueous hydrochloric acid (1 part conc. HCl to 2 parts water) was added until the pH of the solution was approximately 2. Ethyl acetate/diethyl ether (1:1), 20 ml, was added and the system stirred at ambient temperature. The aqueous phase was recovered and extracted with additional 2×20 ml aliquots of ethyl acetate/diethyl ether (1:1). The combined organic layers were washed with 2×5 ml of water, dried over anhydrous sodium sulfate and filtered. Solvent was removed under reduced pressure to yield a crude residue of the captioned acid.

At this point the acid may be recovered and purified by conventional means such as by extraction, chromatography and the like.

Alternatively, however, without further purification the crude acid was transferred to a reaction flask in 45 ml of dimethylformamide. To this solution was added 1.65 g of powdered sodium bicarbonate followed by 2.9 ml of methyl iodide.

This solution was stirred at 45° C. for 48 hours or until esterification was completed. The reaction mixture was filtered through celite. The filter cake was washed with 50 ml of methylene chloride and the combined organic solvents were evaporated under reduced pressure to afford an oily residue. This residue was taken up in 65 ml of methylene chloride which was washed with 2×15 ml of water. The aqueous layer was back-extracted with methylene chloride which was combined with the other methylene chloride solution, dried over anhydrous sodium sulfate and filtered. Removal of the solvent afforded a crude methyl ester which was further purified chromatographically on silica gel. Chromatographic purification was effected using a hexane/50% ethyl acetate-hexane gradient, 75% ethyl acetate-hexane and finally ethyl acetate, as needed. Fractions containing the pure methyl ester were combined and the solvent removed under reduced pressure to give the captioned compound.

This procedure will also serve to convert the other nitrile compounds prepared in Example 13 to their corresponding 9-hydroxy-dienoic methyl esters, illustrated by the following compounds:

methyl 9α-hydroxy-11α,15α-bis-(tetrapyran-2-yloxy)-16-m-trifluoromethylphenoxy-17,18,19,20-tetranorprosta-4,5,13(E)trienoate;

methyl 9α-hydroxy-11α,15α-bis-(tetrapyran-2-yloxy)-16-m-fluorophenoxy-17,18,19,20-tetranorprosta-4,5,13(E)-trienoate;

methyl 9α-hydroxy-11α,15α-bis-(tetrapyran-2-yloxy)16-o-fluorophenoxy-17,18,19,20-tetranorprosta-4,5,13(E)-trienoate;

methyl 9α-hydroxy-11α,15α-bis-(tetrapyran-2-yloxy)-16-p-fluorophenoxy-17,18,19,20-tetranorprosta-4,5,13(E)-trienoate;

methyl 9α-hydroxy-11α,15α-bis-(tetrapyran-2-yloxy)-16-p-chlorophenoxy-17,18,19,20-tetranorprosta-4,5,13(E)-trienoate;

methyl 9α-hydroxy-11α,15α-bis-(tetrapyran-2-yloxy)-16-o-chlorophenoxy-17,18,19,20-tetranorprosta-4,5,13(E)-trienoate;

methyl 9α-hydroxy-11α,15αbis-(tetrapyran-2-yloxy)-16-m-chlorophenoxy-17,18,19,20-tetranorprosta-4,5,13(E)-trienoate;

methyl 9α-hydroxy-11α,15α-bis-(tetrapyran-2-yloxy)-16-m-bromophenoxy-17,18,19,20-tetranorprosta-4,5,13(E)-trienoate;

methyl 9α-hydroxy-11α,15α-bis-(tetrapyran-2-yloxy)-16-o-bromophenoxy-17,18,19,20-tetranorprosta-4,5,13(E)-trienoate;

methyl 9α-hydroxy-11α,15α-bis-(tetrapyran-2-yloxy)-16-p-bromophenoxy-17,18,19,20-tetranorprosta-4,5,13(E)-trienoate;

methyl 9α-hydroxy-11α,15α-bis-(tetrapyran-2-yloxy)-16-p-methylphenoxy-17,18,19,20-tetranorprosta-4,5,13(E)-trienoate;

methyl 9α-hydroxy-11α,15α-bis-(tetrapyran-2-yloxy)-16-o-methylphenoxy-17,18,19,20-tetranorprosta-4,5,13(E)-trienoate;

methyl 9α-hydroxy-11α,15α-bis-(tetrapyran-2-yloxy)-16-m-methylphenoxy-17,18,19,20-tetranorprosta-4,5,13(E)-trienoate;

methyl 9α-hydroxy-11α,15α-bis-(tetrapyran-2-yloxy)-16m-methoxyphenoxy-17,18,19,20-tetranorprosta-4,5,13(E)-trienoate;

methyl 9α-hydroxy-11α,15α-bis-(tetrapyran-2-yloxy)-16-o-methoxyphenoxy-17,18,19,20-tetranorprosta-4,5,13(E)-trienoate;

methyl 9α-hydroxy-11α,15α-bis-(tetrapyran-2-yloxy)-16-p-methoxyphenoxy-17,18,19,20-tetranorprosta-4,5,13(E)-trienoate;

methyl 9α-hydroxy-11α,15α-bis-(tetrapyran-2-yloxy)-16-p-hexylphenoxy-17,18,19,20-tetranorprosta-4,5,13(E)-trienoate;

methyl 9α-hydroxy-11α,15α-bis-(tetrapyran-2-yloxy)-16-o-hexylphenoxy-17,18,19,20-tetranorprosta-4,5,13(E)-trienoate;

methyl 9α-hydroxy-11α,15α-bis-(tetrapyran-2-yloxy)-16-m-hexlphenoxy-17,18,19,20-tetranorprosta-4,5,13(E)-trienoate;

methyl 9α-hydroxy-11α,15α-bis-(tetrapyran-2-yloxy)-16-m-hexyloxyphenoxy-17,18,19,20-tetranorprosta-1(E)-buten-1-yl)-cyclopent-2α-yl)-6-hexa-3,4-dieno-1-nitrile;

methyl 9α-hydroxy-11α,15α-bis-(tetrapyran-2-yloxy)-16-o-hexyloxyphenoxy-17,18,19,20-tetranorprosta-4,5,13(E)-treinoate;

methyl 9α-hydroxy-11α,15α-bis-(tetrapyran-2-yloxy)-16-p-hexyloxyphenoxy-17,18,19,20-tetranorprosta-4,5,13(E)-trienoate;

9α-hydroxy-11α,15α-bis-(tetrahydropyran-2-yloxy)-16-phenoxy-17,18,19,20-tetranorprosta-4,5,13(E)-trienoic acid;

9α-hydroxy-11α,15α-bis-(tetrahydropyran-2-yloxy)-16-o-fluorophenoxy-17,18,19,20-tetranorprosta-4,5,13(E)-trienoic acid;

9α-hydroxy-11α,15α-bis-(tetrahydropyran-2-yloxy)-16-p-fluorophenoxy-17,18,19,20-tetranorprossta-4,5,13(E)-trienoic acid;

9α-hydroxy-11α,15α-bis-(tetrahydropyran-2-yloxy)-16-m-fluorophenoxy-17,18,19,20-tetranorprosta-4,5,13(E)-trienoic acid;

9α-hydroxy-11α,15α-bis-(tetrahydropyran-2-yloxy)-16-m-methylphenoxy-17,18,19,20-tetranorprosta-4,5,13(E)-trienoic acid;

9α-hydroxy-11α,15α-bis-(tetrahydropyran-2-yloxy)-16-p-methylphenoxy-17,18,19,20-tetranorprosta-4,5,13-(E)-trienoic acid;

9α-hydroxy-11α,15α-bis-(tetrahydropyran-2-yloxy)-16-p-methoxyphenoxy-17,18,19,20-tetranorprosta-4,5,13(E)-trienoic acid;

9α-hydroxy-11α,15α-bis-(tetrahydropyran-2-yloxy)-16-o-methoxyphenoxy-17,18,19,20-tetranorprosta-4,5,13(E)-trienoic acid; and 9α-hydroxy-11α,15α-bis-(tetrahydropyran-2-yloxy)-16-p-methoxyphenoxy-17,18,19,20-tetranorprosta-4,5,13(E)-trienoic acid.

EXAMPLE 15

Methyl 9α-oxo-11α,15α-bis-(tetrahydropyran-2-yloxy)-16-phenoxy-17,18,19,20-tetranorprosta-4,5,13(E)-trienoate To a suspension of chromium trioxide (2.66 g) in methylene chloride (100 ml) cooled to about −20° C. was added solid 3,5-dimethylpyrazole (2.58 g) under dry nitrogen. After stirring for approximately ½ hour at −20° C., 3.37 g of methyl 9α-hydroxy-11α,15α-bis-(tetrahydropyran-2-yloxy)-16-phenoxy-17,18,19,20-tetranorprosta-4,5,13(E)-trienoate dissolved in 50 ml of methylene chloride was added. Stirring was continued at the reduced temperature for approximatey 1 hour. Silica gel (50 g) was then added and the solvent removed under reduced pressure. The impregnated silica gel was charged onto the top of a silica gel column made up in hexane. Recovery and separation of the title compound was effected by a 5%-50% gradient of ethyl acetate in hexane. Combined appropriate fractions were concentrated under reduced pressure to give the title compound.

Proceeding in a similar manner, but substituting the appropriate methyl ester of free acid prepared in Example 14 for the 16-phenoxy-substituted compound herein above, all compounds prepared in Example 14 are converted to their corresponding C-9 oxo compound as illustrated by the following compounds:

methyl 9-oxo-11α,15α-bis-(tetrapyran-2-yloxy)-16-m-trifluoromethylphenoxy-17,18,19,20-tetranorprosta-4,5,13(E)trienoate;

methyl 9-oxo-11α,15α-bis-(tetrapyran-2-yloxy)-16-m-fluorophenoxy-17,18,19,20-tetranorprosta-4,5,13(E)-trienoate;

methyl 9-oxo-11α,15α-bis-(tetrapyran-2-yloxy)-16-o-fluorophenoxy-17,18,19,20-tetranorprosta-4,5,13(E)-trienoate;

methyl 9-oxo-11α,15α-bis-(tetrapyran-2-yloxy)-16-p-fluorophenoxy-17,18,19,20-tetranorprosta-4,5,13(E)-trienoate;

methyl 9-oxo-11α,15α-bis-(tetrapyran-2-yloxy)-16-p-chlorophenoxy-17,18,19,20-tetranorprosta-4,4,13(E)-trienoate;

methyl 9-oxo-11α,15α-bis-(tetrapyran-2-xyloxy)-16-o-chlorophenoxy-17,18,19,20-tetranorprosta-4,5,13(E)-trienoate;

methyl 9-oxo-11α,15α-bis-(tetrapyran-2-yloxy)-16-m-chlorophenoxy-17,18,19,20-tetranorprosta-4,5,13(E)-trienoate;

methyl 9-oxo-11α,15α-bis-(tetrapyran-2-yloxy)-16-m-bromophenoxy-17,18,19,20-tetranorprosta-4,5,13(E)-trienoate;

methyl 9-oxo-11α,15α-bis-(tetrapyran-2-yloxy)-16-o-bromophenoxy-17,18,19,20-tetranorprosta-4,5,13(E)-trienoate;

methyl 9-oxo-11α,15α-bis-(tetrapyran-2-yloxy)-16-p-bromophenoxy-17,18,19,20-tetranorprosta-4,5,13(E)-trienoate;

methyl 9-oxo-11α,15α-bis-(tetrapyran-2-yloxy)-16-p-methylphenoxy-17,18,19,20-tetranorprosta-4,5,13(E)-trienoate;

methyl 9-oxo-11α,15α-bis-(tetrapyran-2-yloxy)-16-o-methylphenoxy-17,18,19,20-tetranorprosta-4,5,13(E)-trienoate;

methyl 9-oxo-11α,15α-bis-(tetrapyran-2-yloxy)-16-m-methylphenoxy-17,18,19,20-tetranorprosta-4,5,13(E)-trienoate;

methyl 9-oxo-11α,15α-bis-(tetrapyran-2-yloxy)-16-m-methoxyphenoxy-17,18,19,20-tetranorprosta-4,5,13(E)-trienoate;

methyl 9-oxo-11α,15α-bis-(tetrapyran-2-yloxy)-16-o-methoxyphenoxy-17,18,19,20-tetranorprosta-4,5,13(E)-trienoate;

methyl 9-oxo-11α,15α-bis-(tetrapyran-2-yloxy)-16-p-methoxyphenoxy-17,18,19,20-tetranorprosta-4,5,13(E)-trienoate;

methyl 9-oxo-11α,15α-bis-(tetrapyran-2-yloxy)-16-p-hexylphenoxy-17,18,19,20-tetranorprosta-4,5,13(E)-trienoate;
methyl 9-oxo-11α,15α-bis-(tetrapyran-2-yloxy)-16-o-hexylphenoxy-17,18,19,20-tetranorprosta-4,5,13(E)-trienoate;
methyl 9-oxo-11α,15α-bis-(tetrapyran-2-yloxy)-16-m-hexylphenoxy-17,18,19,20-tetranorprosta-4,5,13(E)-trienoate;
methyl 9-oxo-11α,15α-bis-(tetrapyran-2-yloxy)-16-m-hexyloxyphenoxy-17,18,19,20-tetranorprosta-4,5,13(E)-trienoate;
methyl 9-oxo-11α,15α-bis-(tetrapyran-2-yloxy)-16-o-hexyloxyphenoxy-17,18,19,20-tetranorprosta-4,5,13(E)-treinoate;
methyl 9-oxo-11α,15α-bis-(tetrapyran-2-yloxy)-16-p-hexyloxyphenoxy-17,18,19,20-tetranorprosta-4,5,13(E)-trienoate;
9-oxo-11α,15α-bis-(tetrahydropyran-2-yloxy)-16-phenoxy-17,18,19,20-tetranorprosta-4,5,13(E)-trienoate;
9-oxo-11α,15α-bis-(tetrahydropyran-2-yloxy)-16-o-fluorophenoxy-17,18,19,20-tetranorprosta-4,5,13(E)-trienoate;
9-oxo-11α,15α-bis-(tetrahydropyran-2-yloxy)-16-p-fluorophenoxy-17,18,19,20-tetranorprosta-4,5,13(E)-trienoate;
9-oxo-11α,15α-bis-(tetrahydropyran-2-yloxy)-16-m-fluorophenoxy-17,18,19,20tetranorprosta-4,5,13(E)-trienoate;
9-oxo-11α,15α-bis-(tetrahydropyran-2-yloxy)-16-m-methylphenoxy-17,18,19,20-tetranorprosta-4,5,13(E)-trienoate;
9-oxo-11α,15α-bis-(tetrahydropyran-2-yloxy)-16-p-methylphenoxy-17,18,19,20-tetranorprosta-4,5,13(E)-trienoate;
9-oxo-11α,15α-bis-(tetrahydropyran-2-yloxy)-16-p-methoxyphenoxy-17,18,19,20-tetranorprosta-4,5,13(E)-trienoate;
9-oxo-11α,15α-bis-(tetrahydropyran-2-yloxy)-16-o-methoxyphenoxy-17,18,19,20-tetranorprosta-4,5,13(E)-trienoate; and
9-oxo-11α,15α-bis-(tetrahydropyran-2-yloxy)-16-p-methoxyphenoxy-17,18,19,20-tetranorprosta-4,5,13(E)-trienoate.

EXAMPLE 16

Methyl 9-oxo-11α,15α-bis-(tetrahydropyran-2-yloxy)-16-phenoxy-17,18,19,20-tetranorprosta-4,5,13(E)-trienoate A 0.3 mg aliquot of 9-oxo-11α,15α-bis-(tetrahydropyran-2-yloxy)-16-phenoxy-17,18,19,20-tetranorprosta-4,5,13(E)-trienoic acid was dissolved in 10 ml of anhydrous diethyl ether to which was added an excess of diazomethane at room temperature. The reaction was followed by tlc and when complete, the ether and excess diazomethane was removed under vacuum to give the captioned methyl ester. Proceeding in the same manner, all the 9-oxo acid compounds prepared in Example 15 are converted to their corresponding methyl ester as illustrated by the following compounds:
methyl 9-oxo-11α,15α-bis-(tetrapyran-2-yloxy)-16-m-trifluoromethylphenoxy-17,18,19,20-tetranorprosta-4,5,13(E)trienoate;
methyl 9-oxo-11α,15α-bis-(tetrapyran-2-yloxy)-16-m-fluorophenoxy-17,18,19,20-tetranorprosta-4,5,13(E)-trienoate;
methyl 9-oxo-11α,15α-bis-(tetrapyran-2-yloxy)-16-o-fluorophenoxy-17,18,19,20-tetranorprosta-4,5,13(E)-trienoate;
methyl 9-oxo-11α,15α-bis-(tetrapyran-2-yloxy)-16-p-fluorophenoxy-17,18,19,20-tetranorprosta-4,5,13(E)-trienoate;
methyl 9-oxo-11α,15α-bis-(tetrapyran-2-yloxy)-16-p-chlorophenoxy-17,18,19,20-tetranorprosta-4,5,13(E)-trienoate;
methyl 9-oxo-11α,15α-bis-(tetrapyran-2-yloxy)-16-o-chlorophenoxy-17,18,19,20-tetranorprosta-4,5,13(E)-trienoate;
methyl 9-oxo-11α,15α-bis-(tetrapyran-2-yloxy)-16-m-chlorophenoxy-17,18,19,20-tetranorprosta-4,5,13(E)-trienoate;
methyl 9-oxo-11α,15α-bis-(tetrapyran-2-yloxy)-16-m-bromophenoxy-17,18,19,20-tetranorprosta-4,5,13(E)-trienoate;
methyl 9-oxo-11α,15α-bis-(tetrapyran-2-yloxy)-16-o-bromophenoxy-17,18,19,20-tetranorprosta-4,5,13(E)-trienoate;
methyl 9-oxo-11α,15αbis-(tetrapyran-2-yloxy)-16-p-bromophenoxy-17,18,19,20-tetranorprosta-4,5,13(E)-trienoate;
methyl 9-ox-11α,15α-bis-(tetrapyran-2-yloxy)-16-p-methylpheoxy-17,18,19,20-tetranorprosta-4,5,13(E)-trienoate;
methyl 9-ox-11α,15α-bis-(tetrapyran-2-yloxy)-16-o-methylpheoxy-17,18,19,20-tetranorprosta-4,5,13(E)-trienoate;
methyl 9-oxo-11α,15α-bis-(tetrapyran-2-yloxy)-16-m-methylpheoxy-17,18,19,20-tetranorprosta-4,5,13(E)-trienoate;
methyl 9-oxo-11α,15α-bis-(tetrapyran-2-yloxy-16-m-methoxyphenoxy-17,18,19,20-tetranorprosta-4,5,13(E)-trienoate;
methyl 9-oxo-11α,15α-bis-(tetrapyran-2-yloxy)-16-o-methoxyphenoxy-17,18,19,20-tetranorprosta-4,5,13(E)-trienoate; and
methyl 9-oxo-11α,15α-bis-(tetrapyran-2-yloxy)-16-p-methoxyphenoxy-17,18,19,20-tetranorprosta-4,5,13(E) -trienoate.

EXAMPLE 17

Methyl 9-oxo-11α,15α-dihydroxy-16-phenoxy-17,18,19,20-tetranorprosta-4,5,13(E) -trienoate A 0.3 mg aliquot of the protected methyl ester of Example 15 was dissolved in a solution of glacial acetic acid (10.0 ml), water (6.0 ml) and tetrahydrofuran (1.7 ml). This reaction mixture was stirred for 12 hours at about 40° C. under dry nitrogen. The solvents were removed under reduced pressure. The resulting residue was subjected to azeotropic distillation with toluene (3×10 ml). Further purification was effected on a silica gel column made up in hexane, the product being eluted with 75% ethyl acetate in hexane. Appropriate fractions were combined and evaporated to dryness under reduced pressure to give the title compound.

Proceeding in a similar manner, the esters prepared in Examples 15 and 16 are converted to their corresponding dihydroxy compound as illustrated by the following compounds:
methyl 9-oxo-11α,15α-dihydroxy-16-m-trifluoromethylphenoxy-17,18,19,20-tetranorprosta-4,5,13(E)-trienoate;

methyl 9-oxo-11α,15α-dihydroxy-16-m-fluorophenoxy-17,18,19,20-tetranorprosta-4,5,13(E)-trienoate;
methyl 9-oxo-11α,15α-dihydroxy-16-o-fluorophenoxy-17,18,19,20-tetranorprosta-4,5,13(E)-trienoate;
methyl 9-oxo-11α,15α-dihydroxy-16-p-fluorophenoxy-17,18,19,20-tetranorprosta-4,5,13(E)-trienoate;
methyl 9-oxo-11α,15α-dihydroxy-16-p-chlorophenoxy-17,18,19,20-tetranorprosta-4,5,13(E)-trienoate;
methyl 9-oxo-11α,15α-dihydroxy-16-o-chlorophenoxy-17,18,19,20-tetranorprosta-4,5,13(E)-trienoate;
methyl 9-oxo-11α,15α-dihydroxy-16-m-chlorophenoxy-17,18,19,20-tetranorprosta-4,5,13(E)-trienoate;
methyl 9-oxo-11α,15α-dihydroxy-16-m-bromophenoxy-17,18,19,20-tetranorprosta-4,5,13(E)-trienoate;
methyl 9-oxo-11α,15α-dihydroxy-16-o-bromophenoxy-17,18,19,20-tetranorprosta-4,5,13(E)-trienoate;
methyl 9-oxo-11α,15α-dihydroxy-16-p-bromophenoxy-17,18,19,20-tetranorprosta-4,5,13(E)-trienoate;
methyl 9-oxo-11α,15α-dihydroxy-16-p-methylphenoxy-17,18,19,20-tetranorprosta-4,5,13(E)-trienoate;
methyl 9-oxo-11α,15α-dihydroxy-16-o-methylphenoxy-17,18,19,20-tetranorprosta-4,5,13(E)-trienoate;
methyl 9-oxo-11α,15α-dihydroxy-16-m-methylphenoxy-17,18,19,20-tetranorprosta-4,5,13(E)-trienoate;
methyl 9-oxo-11α,15α-dihydroxy-16-m-methoxyphenoxy-17,18,19,20-tetranorprosta-4,5,13(E)-trienoate;
methyl 9-oxo-11α,15α-dihydroxy-16-o-methoxyphenoxy-17,18,19,20-tetranorprosta-4,5,13(E)-trienoate;
methyl 9-oxo-11α,15α-dihydroxy-16-p-methoxyphenoxy-17,18,19,20-tetranorprosta-4,5,13(E)-trienoate;
methyl 9-oxo-11α,15α-dihydroxy-16-p-hexylphenoxy-17,18,19,20-tetranorprosta-4,5,13(E)-trienoate;
methyl 9-oxo-11α,15α-dihydroxy-16-o-hexylphenoxy-17,18,19,20-tetranorprosta-4,5,13(E)-trienoate;
methyl 9-oxo-11α,15α-dihydroxy-16-m-hexylphenoxy-17,18,19,20-tetranorprosta-4,5,13(E)-trienoate;
methyl 9-oxo-11α,15α-dihydroxy-16-m-hexyloxyphenoxy-17,18,19,20-tetranorprosta-4,5,13(E)-trienoate;
methyl 9-oxo-11α,15α-dihydroxy)-16-o-hexyloxyphenoxy-17,18,19,20-tetranorprosta-4,5,13(E)-treinoate; and
methyl 9-oxo-11α,15α-dihydroxy)-16-p-hexyloxyphenoxy-17,18,19,20-tetranorprosta-4,5,13(E)-trienoate.

This procedure may also be used to hydrolytically cleave the ether groups of any of the intermediates set out herein in the foregoing examples.

EXAMPLE 18

Methyl 9-oxo-11α,15α-dihydroxy-16-phenoxy-17,18,19,20-tetranorprosta-4,5,13(E)-trienoate A 500 mg aliquot of the protected methyl ester prepared in Example 15 was dissolved in methylene chloride and 0.1 ml of 48% hydrofluoric acid added with vigorous stirring. There was then added dropwise, 7.5 ml of a methylene chloride solution of mercaptoethanol (17 mg/ml) over 30 minutes. The solution was then neutralized with approximately 0.3 ml of aqueous sodium bicarbonate. Methylene chloride was used to extract the product. The combined extracts were dried with sodium sulfate, the solvent removed under reduced pressure and the product purified using a silica gel column. The column was eluted in steps with 20% ethyl acetate/hexane, 50% and 75% ethyl acetate/hexane and finally ethyl acetate. As in Example 17, all alkyl ester compounds prepared in Examples 15 and 16 may be hydrolyzed by the foregoing procedure.

EXAMPLE 19

Methyl 9-oxo-15α-hydroxy-16-phenoxy-17,18,19,20-tetranorprosta-4,5,10,13(E)-tetraenoate A 4.91 g. sample of the methyl ester from Example 18 was dissolved in a solvent made up of 286 ml of glacial acetic acid and 32 ml of water. The solution was heated at 65° C. overnight. The solvents were then stripped off under reduced pressure. Toluene, 25 ml, was then added and stripped off under vacuum, this procedure being repeated twice. The resulting residue was vacuum dried yielding an oil. This oil was partitioned between 330 ml of diethyl ether and 83 ml of water. The organic layer was washed with brine and dried over sodium sulfate. The ether was stripped off and the resulting oil percolated through silica gel prepared in 20% ethyl acetate/hexane. This column was then eluted with 20% ethyl acetate/hexane (600 ml) 25% ethyl acetate/hexane (2000 ml) 30% ethyl acetate/hexane (500 ml) and 35% ethyl acetate/hexane (500 ml). Combination of appropriate fractions gave the title compound as a colorless oil after the solvent had been removed.

EXAMPLE 20

Methyl 9-oxo-15α-(tetrahydropyran-2-yloxy)-16-phenoxy-17,18,19,20-tetranorprosta-4,5,10,13(E)-tetraenoate A 250 ml round bottom flask equipped with a magnetic stirring bar and Drierite® drying tube was charged with 6.30 g of the compound from Example 19 in 90 ml of dry tetrahydrofuran. To this was added 36 ml of dihydropyran and 60 ml of p-toluene sulfonic acid ~H2O. This mixture was stirred at room temperature for approximately one hour at which time 600 mg of powdered sodium bicarbonate was added. This mixture was stirred for approximately 15 minutes whereupon 300 ml of water and 100 ml of ethyl acetate were added. The ethyl acetate layer was recovered and the aqueous layer extracted twice more with 30 ml of ethyl acetate. The combined organic layers were washed with 30 ml of saturated aqueous sodium bicarbonate, 2×30 ml of water and 1×60 ml of brine. The ethyl acetate was then dried over sodium sulfate, filtered, and concentrated to give a yellow oil. This oil was further purified on a silica gel column packed wet in 10% ethyl acetate/hexane. The title product was eluted using 2600 ml of 10% ethyl acetate/hexane followed by 2400 ml o 20% ethyl acetate hexane. Appropriate fractions were combined and concentrated to give the title compound as a light-colored oil.

EXAMPLE 21

Ethyl 9-hydroxy-15α-(tetrahydropyran-2-yloxy)-16-phenoxy-17,18,19,20-tetranorprosta-4,5,13(E)-trienoate To a stirred solution of 250 mg methyl 9-oxo-15α-(tetrahydropyran-2-yloxy)-16-phenoxy-17,18,19,20-tetranorprosta-4,5,10,13(E)-tetraenoate in absolute ethanol was added 1.07 ml of a solution of 0.84 g of sodium borohydride in 22.2 ml of absolute ethanol at room temperature. After stirring this solution for 30 minutes at room temperature, heat was applied to the solution by means of a steam bath. Heating was continued for 3 hours after which 0.5 ml more of the sodium borohydride reagent was added. This solution was stirred for an additional 15 minutes as the solution cooled. Acetone was then added drop-wise to consume excess borohydride. This solution was stirred until cool at which time 10 ml of saturated aqueous ammonium chloride and 4 ml diethyl ether were added with stirring. The aqueous layer was extracted with 2×4 ml of diethyl ether. The combined organic layers were washed with 1×2 ml of water, 1×2 ml of brine, and dried over sodium sulfate. The dried solution was filtered and concentrated in vacuo to give the title compound as a colorless oil.

EXAMPLE 22

Ethyl 9-oxo-15α-(tetrahydropyran-2-yloxy)-16-phenoxy-17,18,19,20-tetranorprosta-4,5,13(E)-trienoate To 0.29 g of dry chromium tiroxide under nitrogen was added 4.9 ml of methylene chloride. This solution was cooled to −20° C. and 0.29 g of 3,5-dimethylpyrazole added with stirring. Stirring was continued for 30 minutes at which time 0.22 mg of ethyl 9-oxo-15α-(tetrahydropyran-2-yloxy)-16-phenoxy-17,18,19,20-tetranorprosta-4,5,13(E)-tetraenoate in 1.5 ml of methylene chloride was added with 2×1 ml methylene chloride washes. Stirring was continued for 1 hour at −20° C., then one hour at room temperature. The reaction solution was transfered to a larger flask and 1.1 g of silica gel added and the mixture stripped to dryness. Hexane was added and the mixture again stripped to dryness. The silica gel absorbed product was then placed atop a 5 g column of silica gel packed in 12% ethyl acetate/hexane. The column was eluted with the packing solvent. Fifty 10 ml fractions were collected. Appropriate fractions were combined and stripped to dryness to give the title compound as a yellow oil.

EXAMPLE 23

Methyl 9-oxo-15α-(tetrahydropyran-2-yloxy)-16-phenoxy-17,18,19,20-tetranorprosta-4,5,13(E)-trienoate In 4.5 ml of anhydrous methanol was dissolved 0.13 g of ethyl 9-oxo-15α-(tetrahydropyran-2-yloxy)-16-phenoxy-17,18,19,20-tetranorprosta-4,5,13(E)-trienoate to which was added 1 ml of saturated anhydrous potassium carbonate in absolute methanol. This solution was stirred at room temperature for 20 hours. The methanol was then striped off and 5 ml of diethyl ether and 5 ml of water added to the residue with stirring. The aqueous layer was extracted with 3×5 ml of diethyl ether. Combined organic layers were washed with 10 ml of water, 10 ml of brine and dried over sodium sulfate, filtered and concentrated under vacuum to give the title compound as a colorless oil.

The aqueous layer from above was acidified with 1M oxalic acid (pH=ca. 2). This acidified solution was extracted 3×5 ml with diethyl ether. Combined organic layers were washed with 5 ml of water, 2 ml of brine, dried over sodium sulfate, filtered, and concentrated in vacuo to give an oil. This oil was esterified with diazomethane to give the title compound.

EXAMPLE 24

Methyl 9-oxo-15α-hydroxy-16-phenoxy-17,18,19,20-tetranorprosta-4,5,13(E)-trienoate A 6 ml amount of a 8:1:4 mixture of glacial acetic acid, tetrahydrofuran and water was added to 100 mg of methyl 9-oxo-15α-(tetrahydropyran-2-yloxy)-16-phenoxy-17,18,19,20-tetranorprosta-4,5,13(E)-tetraenoate, which solution was stirred at room temperature overnight. The volatiles were stripped off and 50 ml of toluene added and stripped off twice to give the title compound as a crude product. This crude product was further purified by flash column chromatography on a 6 in×20 mm column silica gel eluting with 47% ethyl acetate/hexane. Appropriate fractions were combined and concentrated in vacuo to give the title compound as a colorless oil. The infrared and mass spectral data for this compound are as follows:

I.R.: 3460, 1970, 1740, 760, 698 cm$^{-1}$.

M.S.: 384 (m$^+$), 366, 311, 291, 283, 277, 273, 259, 199.

Proceeding in the same manner, but substituting the appropriate precursor from the reactions of Examples 18 or 19 through Example 23 for the compound described in the above paragraph, the following compounds are made:

methyl 9-oxo-15α-hydroxy-16-m-trifluoromethylphenoxy-17,18,19,20-tetranorprosta-4,5,13(E)-trienoate;

methyl 9-oxo-15α-hydroxy-16-m-fluorophenoxy-17,18,19,20-tetranorprosta-4,5,13(E)-trienoate;

methyl 9-oxo-15α-hydroxy-16-o-fluorophenoxy-17,18,19,20-tetranorprosta-4,5,13(E)-trienoate;

methyl 9-oxo-15α-hydroxy-16-p-fluorophenoxy-17,18,19,20-tetranorprosta-4,5,13(E)-trienoate;

methyl 9-oxo-15α-hydroxy-16-p-chlorophenoxy-17,18,19,20-tetranorprosta-4,5,13(E)-trienoate;

methyl 9-oxo-15α-hydroxy-16-o-chlorophenoxy-17,18,19,20-tetranorprosta-4,5,13(E)-trienoate;

methyl 9-oxo-15α-hydroxy-16-m-chlorophenoxy-17,18,19,20-tetranorprosta-4,5,13(E)-trienoate;

methyl 9-oxo-15α-hydroxy-16-m-bromophenoxy-17,18,19,20-tetranorprosta-4,5,13(E)-trienoate;

methyl 9-oxo-15α-hydroxy-16-o-bromophenoxy-17,18,19,20-tetranorprosta-4,5,13(E)-trienoate;

methyl 9-oxo-15α-hydroxy-16-p-bromophenoxy-17,18,19,20-tetranorprosta-4,5,13(E)-trienoate;

methyl 9-oxo-15α-hydroxy-16-p-methylphenoxy-17,18,19,20-tetranorprosta-4,5,13(E)-trienoate;

methyl 9-oxo-15α-hydroxy-16-o-methylphenoxy-17,18,19,20-tetranorprosta-4,5,13(E)-trienoate;

methyl 9-oxo-15α-hydroxy-16-m-methylphenoxy-17,18,19,20-4,5,13(E)-trienoate;

methyl 9-oxo-15α-hydroxy-16-m-methoxyphenoxy-17,18,19,20-tetranorprosta-4,5,13(E)-trienoate;

methyl 9-oxo-15α-hydroxy-16-o-methoxy-phenoxy-17,18,19,20-tetranorprosta-4,5,13(E)-trienoate;

methyl 9-oxo-15α-hydroxy-16-p-methoxyphenoxy-17,18,19,20-tetranorprosta-4,5,13(E)-trienoate;

methyl 9-oxo-15α-hydroxy-16-p-hexylphenoxy-17,18,19,20-tetranorprosta-4,5,13(E)-trienoate;

methyl 9-oxo-15α-hydroxy-16-o-hexylphenoxy-17,18,19,20-tetranorprosta-4,5,13(E)-trienoate;

methyl 9-oxo-15α-hydroxy-16-m-hexylphenoxy-17,18,19,20-tetranorprosta-4,5,13(E)-trienoate;

methyl 9-oxo-15α-hydroxy-16-m-hexyloxyphenoxy-17,18,19,20-tetranorprosta-4,5,13(E)-trienoate;

methyl 9-oxo-15α-hydroxy)-16-o-hexyloxyphenoxy-17,18,19,20-tetranorprosta-4,5,13(E)-trienoate; and methyl 9-oxo-15α-hydroxy)-16-p-hexyloxyphenoxy-17,18,19,20-tetranorprosta-4,5,13(E)-trienoate.

Individual alkyl 9-oxo-15α-hydroxy-16-phenoxy-trienoate isomers were prepared by taking a single propargyl alcohol isomer as prepared in Example 9 and carrying that single isomer through the subsequent steps as set out in Examples 10-24.

EXAMPLE 25

Determination of Gastric Juice Flow Inhibition

Materials and Methods

Hilltop, Sprague-Dawley derived male rats (200-250 g) were starved in individual cages for 48 hours prior to the experiment. A circular, plastic collor was stapled arount the neck of each rat to "prevent" coprophagy and hair ingestion. Water was available ad libitum. During the morning of the experiment, after 48 hours of starvation, the test compound was administered 30 minutes prior to surgery. The test compound was administered orally (p.o.). After compound administration, rats were anesthetized with ether, a ligature was placed and tied around the esophagus to prevent saliva from draining into the stomach. Midline laparotomy was performed to expose the stomach and a ligature was tied around the duodenum near the pyloric sphincter of the stomach. Incisions were then closed with wound clips and the animal injected with histamine, 40 mg/Kg, subcutaneously once during the 3-hour experimental period. At the end of 3 hours, the rats were killed, gastric juice was completely aspirated from the stomach and volume recorded. An aliquot of this juice was titrated with 0.02N sodium hydroxide to pH 7.0±0.1, using a Beckman pH meter to determine the end point. The milliequivalents of hydrogen chloride per 100 g of body weight were calculated. The pH was also recorded. Each dose of a test compouns was investigated in 8-10 rats. Statistical evaluation was done using Student's t-test.

What is claimed is:

1. A compound of the formula

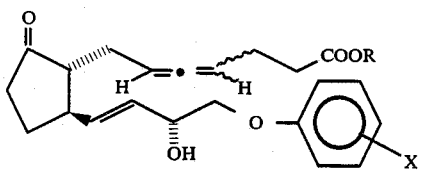

or a racemic mixture thereof wherein R is hydrogen, lower alkyl or a pharmaceutically acceptable, non-toxic salt of a compound wherein R is hydrogen; X is hydrogen, halo, trifluoromethyl, lower alkyl or lower alkoxy; and the wavy lines represent the α or β configuration with the proviso that when one wavy line is α the other is β.

2. The compound of claim 1 wherein R is methyl, and X is hydrogen namely (dl)-9-oxo-15α-hydroxy-16-phenoxy-17,18,19,20-tetranorprosta-4,5,13(E)-trienoic acid methyl ester.

3. The enantiomer or racemic mixture of the compound of claim 2 represented by the structure

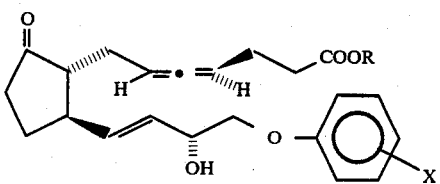

wherein R is methyl and X is hydrogen.

4. The enantiomer or racemic mixture of the compound of claim 2 represented by the structure

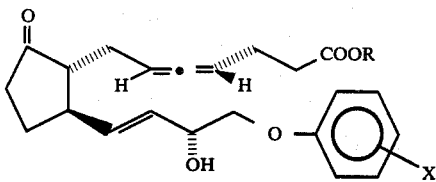

wherein R is methyl and X is hydrogen.

5. A method for reducing gastric acid secretion which method comprises administering to a human a pharmaceutically acceptable composition comprising a pharmaceutically acceptable excipient and a compound of the formula

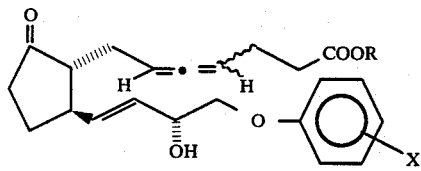

or a racemic mixture thereof wherein R is hydrogen, lower alkyl or a pharmaceutically acceptable, non-toxic salt of a compound wherein R is hydrogen; X is hydrogen, halo, trifluoromethyl, lower alkyl or lower alkoxy; and the wavy lines represent the α or β configuration with the proviso that when one wavy line is α the other is β.

6. The method of claim 5 wherein in the compound of formula (I) R is methyl, and X is hydrogen namely (dl)-9-oxo-15α-hydroxy-16-phenoxy-17,18,19,20-tetranorprosta-4,5,13(E)-trienoic acid methyl ester.

7. The method of claim 6 wherein compound is an enantiomer or racemic mixture of a compound represented by the structure

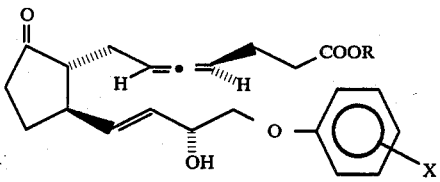

wherein R is methyl and X is hydrogen.

8. The method of claim 6 wherein the compound is an enantiomer or racemic mixture of a compound of the formula represented by the structure

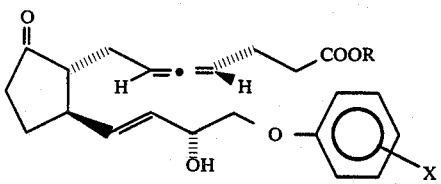

wherein R is methyl and X is hydrogen.

* * * * *

UNITED STATES PATENT AND TRADEMARK OFFICE
CERTIFICATE OF CORRECTION

PATENT NO. : 4,618,696
DATED : October 21, 1986
INVENTOR(S) : GARY F. COOPER, et al.

It is certified that error appears in the above-identified patent and that said Letters Patent is hereby corrected as shown below:

In the Title, "9-OXO-15α-HYDROXY-16-PHENOXY AND 16-SUBSTITUTED PHENOXY 17,18,19,20-TETRANORPROSTA-4,5,13,(E)-TRIENOATES" should read -- 9-OXO-15α-HYDROXY-16-PHENOXY AND 16-SUBSTITUTED PHENOXY 17,18,19, 20-TETRANORPROSTA-4,5,13(E)-TRIENOATES --.

In Column 1, line 11, "hydroxy" should read -- phenoxy --.

In Column 1, line 12, "treinoate" should read -- trienoate --.

In Column 1, line 34, "R'" should read -- R" --.

In Column 1, line 45, "R'" should read -- R" --.

In Column 2, line 23, "flouro" should read -- fluoro --.

In Column 3, line 40, "surprising" should read -- surprisingly --.

In Column 5, formula 3 reading

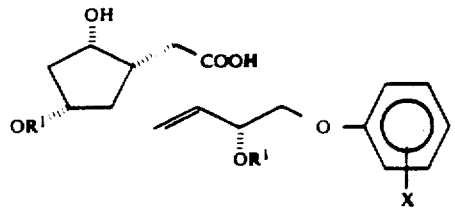 should read 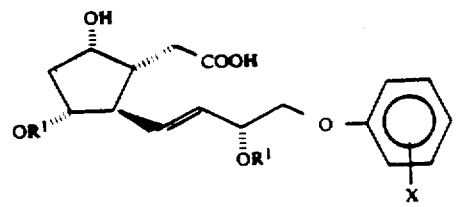

UNITED STATES PATENT AND TRADEMARK OFFICE
CERTIFICATE OF CORRECTION

PATENT NO. : 4,618,696
DATED : October 21, 1986
INVENTOR(S) : GARY F. COOPER, et al.

It is certified that error appears in the above-identified patent and that said Letters Patent is hereby corrected as shown below:

In Column 6, formula 4 reading

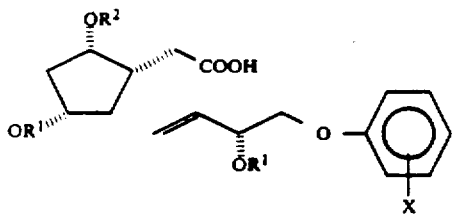   should read   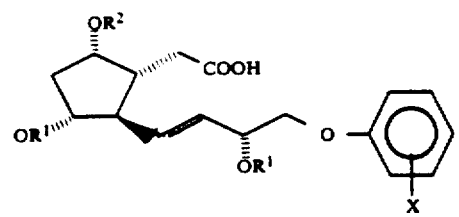

In Column 6, formula 10 reading

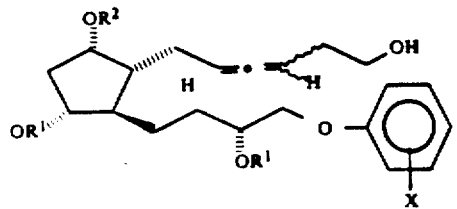   should read   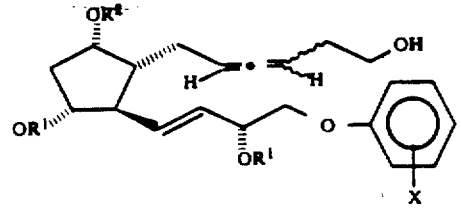

In Column 10, formula 20 reading

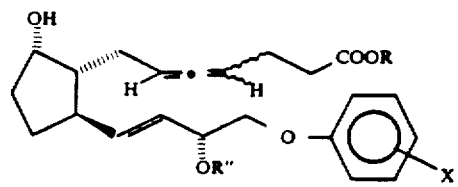   should read   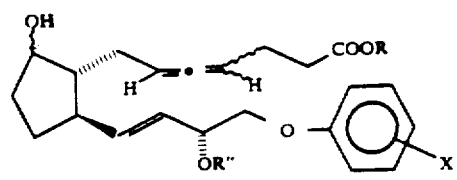

UNITED STATES PATENT AND TRADEMARK OFFICE
CERTIFICATE OF CORRECTION

PATENT NO. : 4,618,696
DATED : October 21, 1986
INVENTOR(S) : GARY F. COOPER, et al.

It is certified that error appears in the above-identified patent and that said Letters Patent is hereby corrected as shown below:

In Column 11, line 36, insert -- a -- after "added to".

In Column 11, line 68, "dimethylforamide" should read -- dimethylformamide --.

In Column 12, line 61, "and the like preferably," should read -- and the like, preferably --.

In Column 13, line 6, "methyl ester" should read -- free acid --.

In Column 16, line 28, "heatein" should read -- heating --.

In Column 16, line 37, "herein above" should read -- hereinabove --.

In Column 21, line 11, "methyl (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetate" should read -- (1α-t-butyldimethylsilyloxy-4α-(tetrahydropyran-2-yloxy)-3β-(3α-(tetrahydropyran-2-yloxy)-4-phenoxy-1(E)-buten-1-yl)cyclopent-2α-yl)acetic acid --.

In Column 21, line 17, "acetate" should read -- acid --.

In Column 23, line 17, "vaccuum" should read -- vacuum --.

In Column 33, lines 22-25, "methyl 9α-hydroxy-11α,15α-bis-(tetrapyran-2-yloxy)-16-m-hexyloxyphenoxy-17,18,19,20-tetranorprosta-1(E)-buten-1-yl)-cyclopent-2α-yl)-6-hexa-3,4-dieno-1-nitrile" should read -- methyl 9α-hydroxy-11α,15α-bis-(tetrapyran-2-yloxy)-16-m-hexyloxyphenoxy-17,18,19,20-tetranorprosta-4,5,13(E)-trienoate --.

In Column 33, line 28, "treinoate" should read -- trienoate --.

UNITED STATES PATENT AND TRADEMARK OFFICE
CERTIFICATE OF CORRECTION

PATENT NO. : 4,618,696
DATED : October 21, 1986
INVENTOR(S) : GARY F. COOPER, et al.

It is certified that error appears in the above-identified patent and that said Letters Patent is hereby corrected as shown below:

In Column 33, line 62, "9α-oxo-11α,15α-bis-(tetrahydropyran-2-yloxy)-16-phenoxy-17,18,19,20-tetranorprosta-4,5,13(E)-trienoate" should read -- 9-oxo-11α,15α-bis-(tetrahydropyran-2-yloxy)-16-phenoxy-17,18,19,20-tetranorprosta-4,5,13(E)-trienoate --.

In Column 35, line 15, "treinoate" should read -- trienoate --.

In Column 39, line 24, "tiroxide" should read -- trioxide --.

In Column 39, line 28, "9-oxo-15α(tetrahydropyran-2-yloxy)-16-phenoxy-17,18,19,20-tetranorprosta-4,5,13(E)-tetranoate" should read -- 9-hydroxy-15α(tetrahydropyran-2-yloxy)-16-phenoxy-17,18,19,20-tetranorprosta-4,5,13(E)-trienoate --.

In Column 40, line 9, "methyl 9-oxo-15α-(tetrahydropyran-2-yloxy)-16-phenoxy-17,18,19,20-tetranorprosta-4,5,13(E)-tetranoate" should read -- methyl 9-oxo-15α-(tetrahydropyran-2-yloxy)-16-phenoxy-17,18,19,20-tetranorprosta-4,5,13(E)-trienoate --.

In Column 40, line 53, "methyl 9-oxo-15α-hydroxy-16-m-methylphenoxy-17,18,19,20-4,5,13(E)-trienoate" should read -- methyl 9-oxo-15α-hydroxy-16-m-methylphenoxy-17,18,19,20-tetranorprosta-4,5,13(E)-trienoate --.

In Column 41, line 1, "methyl 9-oxo-15α-hydroxy)-16-o-hexyloxyphenoxy-17,18,19,20-4,5,13(E)-trienoate" should read -- methyl 9-oxo-15α-hydroxy-16-o-hexyloxyphenoxy-17,18,19,20-tetranorprosta-4,5,13(E)-trienoate --.

UNITED STATES PATENT AND TRADEMARK OFFICE
CERTIFICATE OF CORRECTION

PATENT NO. : 4,618,696
DATED : October 21, 1986
INVENTOR(S) : GARY F. COOPER, et al.

It is certified that error appears in the above-identified patent and that said Letters Patent is hereby corrected as shown below:

In Column 41, line 3, "methyl 9-oxo-15α-hydroxy)-16-p-hexyloxyphenoxy-17,18,19,20-4,5,13(E)-trienoate" should read -- methyl 9-oxo-15α-hydroxy-16-p-hexyloxyphenoxy-17,18,19,20-tetranorprosta-4,5,13(E)-trienoate --.

Signed and Sealed this

Fourth Day of July, 1989

Attest:

DONALD J. QUIGG

Attesting Officer

Commissioner of Patents and Trademarks